United States Patent
Fischell et al.

(10) Patent No.: US 7,801,596 B2
(45) Date of Patent: Sep. 21, 2010

(54) PHYSICIAN'S PROGRAMMER FOR IMPLANTABLE DEVICES HAVING CARDIAC DIAGNOSTIC AND PATIENT ALERTING CAPABILITIES

(75) Inventors: David R. Fischell, Fair Haven, NJ (US); Jonathan Harwood, Rumson, NJ (US); Steven R. Johnson, Fair Haven, NJ (US); Tim A. Fischell, Kalamazoo, MI (US)

(73) Assignee: Angel Medical Systems, Inc., Fair Haven, NJ (US)

( * ) Notice: Subject to any disclaimer, the term of this patent is extended or adjusted under 35 U.S.C. 154(b) by 546 days.

(21) Appl. No.: 11/130,110

(22) Filed: May 17, 2005

(65) Prior Publication Data

US 2006/0265020 A1    Nov. 23, 2006

Related U.S. Application Data

(63) Continuation-in-part of application No. 10/642,245, filed on Aug. 18, 2003, which is a continuation-in-part of application No. 10/251,505, filed on Sep. 20, 2002, now Pat. No. 6,609,023.

(51) Int. Cl.
    *A61B 5/0452* (2006.01)
(52) U.S. Cl. .......................................... 600/523; 607/59
(58) Field of Classification Search ................. 600/517, 600/523; 607/59
    See application file for complete search history.

(56) References Cited

U.S. PATENT DOCUMENTS

| 3,867,950 A | 2/1975 | Fischell |
| 3,888,260 A | 6/1975 | Fischell |
| 4,003,379 A | 1/1977 | Ellinwood, Jr. |
| 4,223,678 A | 9/1980 | Langer et al. |
| 4,295,474 A | 10/1981 | Fischell |
| 4,373,527 A | 2/1983 | Fischell |
| 4,543,955 A | 10/1985 | Schroeppel |
| 4,658,830 A | 4/1987 | Sarnoff |
| 4,796,641 A | 1/1989 | Mills et al. |
| 4,905,707 A | 3/1990 | Davies et al. |
| 5,042,497 A | 8/1991 | Shapland |
| 5,113,869 A | 5/1992 | Nappholz et al. |
| 5,135,004 A | 8/1992 | Adams et al. |
| 5,139,028 A | 8/1992 | Steinhaus et al. |
| 5,199,428 A | 4/1993 | Obel et al. |
| 5,305,745 A | 4/1994 | Zacouto |
| 5,313,953 A | 5/1994 | Yomtov et al. |

(Continued)

OTHER PUBLICATIONS

Warnecke, H., et al., "Clinical Heart Transplantation without Routine Endomycardial Biopsy," The Journal of Heart and Lung Transplantation, vol. 11, No. 6, Nov./Dec. 1992, pp. 1093-1102.

(Continued)

*Primary Examiner*—Carl H Layno
*Assistant Examiner*—Yun Haeng Lee
(74) *Attorney, Agent, or Firm*—Rosenberg, Klein & Lee

(57) ABSTRACT

A programmer is provided for an implantable medical device capable of detecting cardiac events in a human patient. The programmer has a two-way wireless data communication mechanism with the implantable medical device and a graphical user interface is included which has a display and input mechanism designed for use in programming patient specific parameters for the detection of ST shift related cardiac events.

64 Claims, 18 Drawing Sheets

U.S. PATENT DOCUMENTS

| | | | | |
|---|---|---|---|---|
| 5,330,505 A | | 7/1994 | Cohen | |
| 5,402,794 A | | 4/1995 | Wahlstrand et al. | |
| 5,404,877 A | | 4/1995 | Nolan et al. | |
| 5,409,009 A | | 4/1995 | Olson | |
| 5,411,031 A | | 5/1995 | Yomtov | |
| 5,417,717 A | | 5/1995 | Salo et al. | |
| 5,496,351 A | | 3/1996 | Plicchi et al. | |
| 5,497,780 A | | 3/1996 | Zehender | |
| 5,531,768 A | | 7/1996 | Alferness | |
| 5,634,899 A | | 6/1997 | Shapland et al. | |
| 5,724,985 A | * | 3/1998 | Snell et al. | 600/510 |
| 5,730,125 A | | 3/1998 | Prutchi et al. | |
| 5,792,066 A | | 8/1998 | Kwong | |
| 5,800,498 A | | 9/1998 | Obino et al. | |
| 5,876,353 A | | 3/1999 | Riff | |
| 5,925,066 A | | 7/1999 | Kroll et al. | |
| 5,956,013 A | * | 9/1999 | Raj et al. | 345/208 |
| 5,987,352 A | | 11/1999 | Klein et al. | |
| 6,049,736 A | | 4/2000 | Stewart et al. | |
| 6,112,116 A | | 8/2000 | Fischell et al. | |
| 6,122,536 A | | 9/2000 | Sun et al. | |
| 6,126,038 A | | 10/2000 | Olegnowicz | |
| 6,128,526 A | | 10/2000 | Stadler et al. | |
| 6,230,049 B1 | | 5/2001 | Fischell et al. | |
| 6,272,379 B1 | | 8/2001 | Fischell et al. | |
| 6,289,244 B1 | * | 9/2001 | Conley et al. | 607/27 |
| 6,289,248 B1 | * | 9/2001 | Conley et al. | 607/59 |
| 6,368,284 B1 | | 4/2002 | Bardy | |
| 6,393,325 B1 | * | 5/2002 | Mann et al. | 607/46 |
| 6,468,263 B1 | | 10/2002 | Fischell et al. | |
| 6,491,639 B1 | | 12/2002 | Turcott | |
| 6,501,983 B1 | | 12/2002 | Natarajanl et al. | |
| 6,522,926 B1 | | 2/2003 | Kieval et al. | |
| 6,609,023 B1 | | 8/2003 | Fischell et al. | |
| 6,616,624 B1 | | 9/2003 | Kieval | |
| 6,622,045 B2 | * | 9/2003 | Snell et al. | 607/30 |
| 6,850,801 B2 | | 2/2005 | Kieval et al. | |
| 2001/0031997 A1 | | 10/2001 | Lee | |
| 2003/0139778 A1 | | 7/2003 | Fischell et al. | |
| 2004/0059238 A1 | | 3/2004 | Fischell et al. | |
| 2005/0113705 A1 | | 5/2005 | Fischell et al. | |
| 2005/0113886 A1 | | 5/2005 | Fischell et al. | |
| 2005/0137483 A1 | | 6/2005 | Fischell et al. | |
| 2005/0165321 A1 | | 7/2005 | Fischell et al. | |
| 2006/0064136 A1 | | 3/2006 | Wang | |

OTHER PUBLICATIONS

Knosalla, C., et al., "Intramyocardial Electrogram Recordings (IMEG) for Diagnosis of Cellular and Humoral Mediated Cardiac Allograft Rejection", Annals of Thoracic and Cardiovascular Surgery (ATCS), vol. 6, No. 2, 2000, pp. 89-94.

* cited by examiner

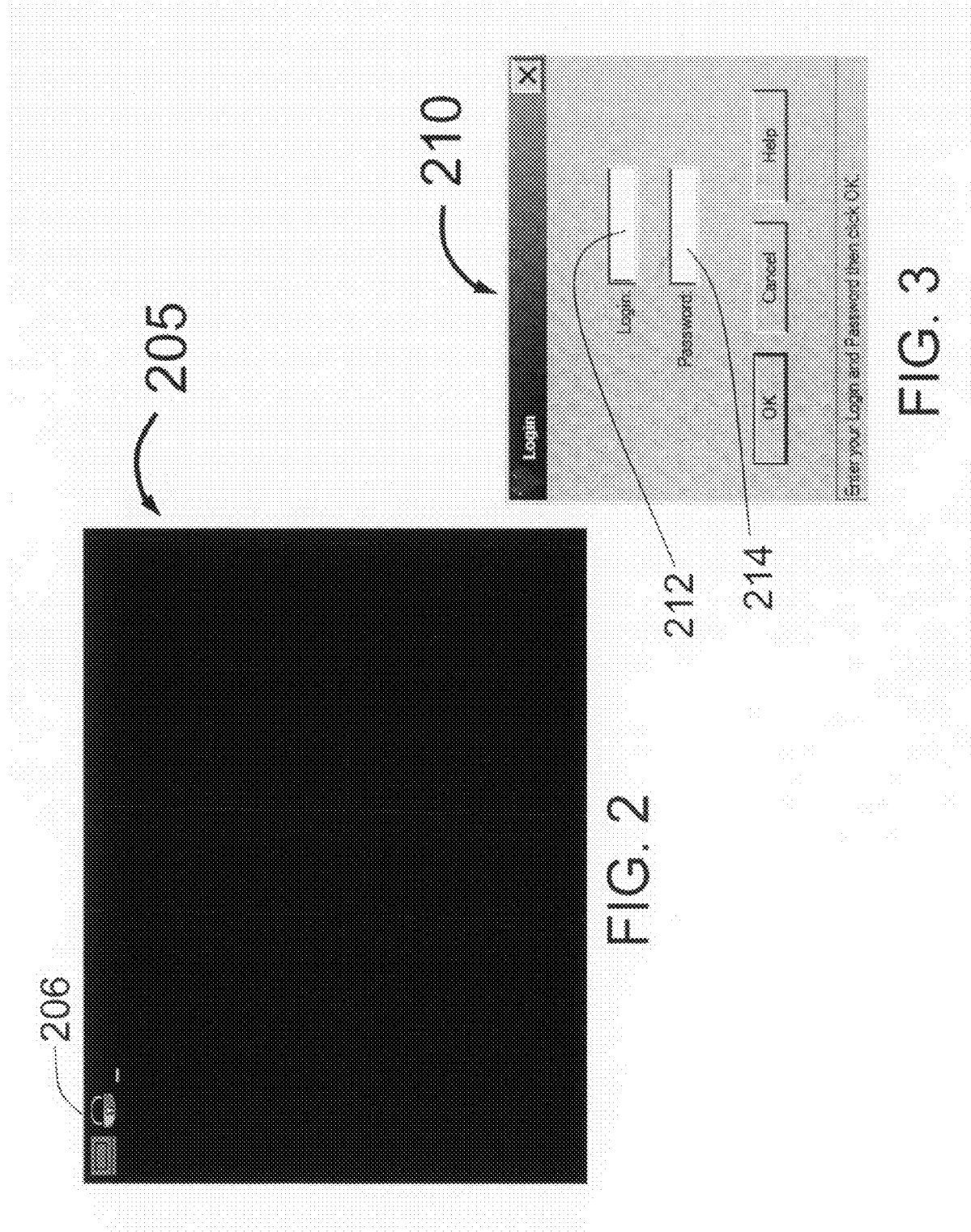

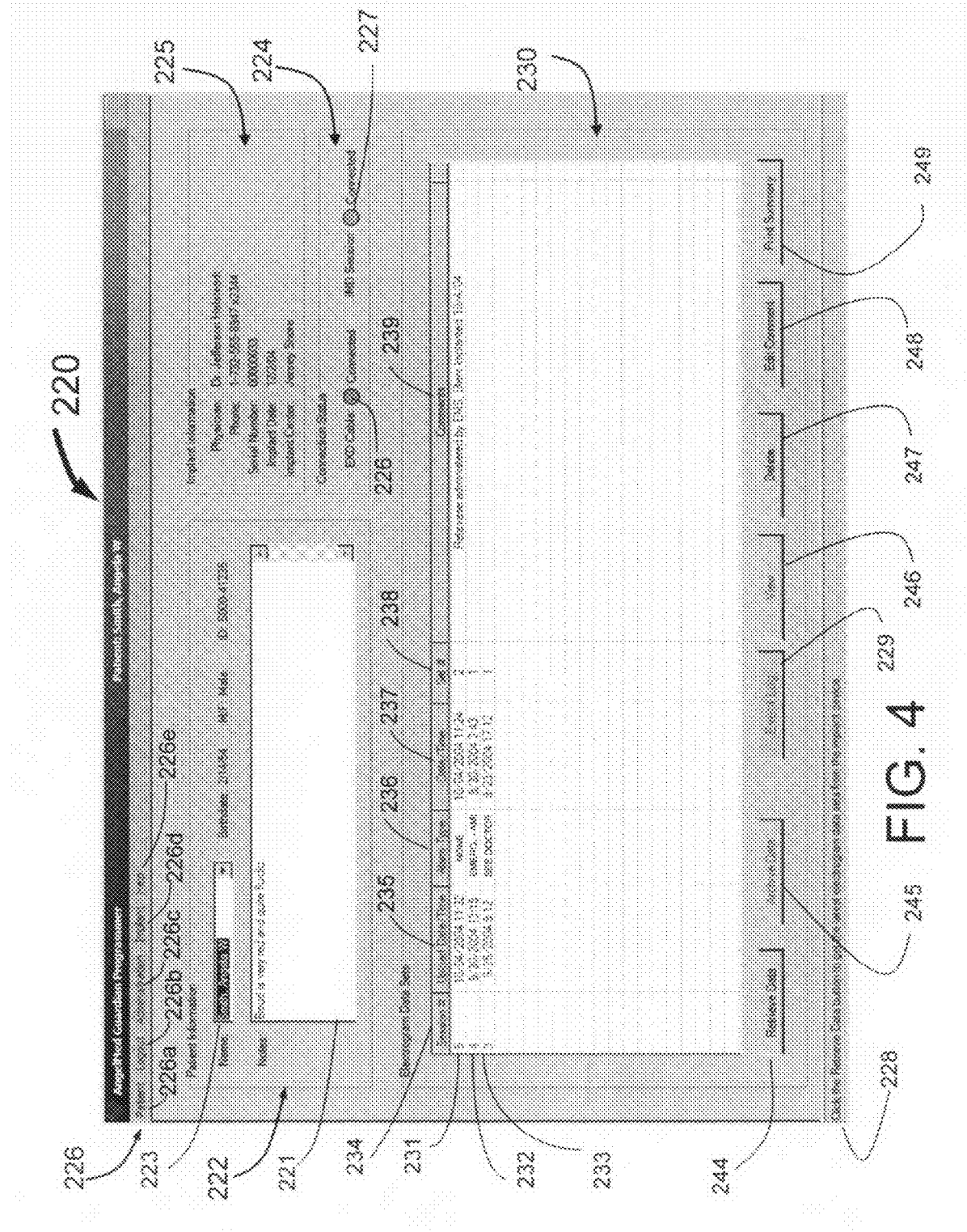

US 7,801,596 B2

PHYSICIAN'S PROGRAMMER FOR IMPLANTABLE DEVICES HAVING CARDIAC DIAGNOSTIC AND PATIENT ALERTING CAPABILITIES

RELATED PATENT APPLICATIONS

This Patent Application is a Continuation-In-Part of patent application Ser. No. 10/642,245 filed on 18 Aug. 2003, now pending which is a Continuation-in-Part of Ser. No. 10/251,505 filed on 20 Sep. 2002 and now issued as U.S. Pat. No. 6,609,023.

FIELD OF USE

This invention is in the field of systems, including devices with diagnostic capabilities implanted within a human patient.

BACKGROUND OF THE INVENTION

Heart disease is the leading cause of death in the United States. A heart attack (also known as an acute myocardial infarction (AMI)) typically results from a thrombus (i.e., a blood clot) that obstructs blood flow in one or more coronary arteries. AMI is a common and life-threatening complication of coronary heart disease. Myocardial ischemia is caused by an insufficiency of oxygen to the heart muscle. Ischemia is typically provoked by physical activity or other causes of increased heart rate when one or more of the coronary arteries are narrowed by atherosclerosis. Patients will often (but not always) experience chest discomfort (angina) when the heart muscle is experiencing ischemia. Those with coronary atherosclerosis are at higher risk for AMI if the plaque becomes further obstructed by thrombus.

The current treatment for a coronary narrowing (a stenosis) is the insertion of a drug-eluting stent such as the Cypher™ sirolimus-eluting stent from Cordis Corp. or the Taxus™ paclitaxel-eluting stent from the Boston Scientific Co.

Acute myocardial infarction and ischemia may be detected from a patient's electrocardiogram (ECG) by noting an ST segment shift (i.e., voltage change) over a relatively short (less than 5 minutes) period of time. However, without knowing the patient's normal ECG pattern, detection from a standard 12-lead ECG can be unreliable.

Fischell et al. in U.S. Pat. Nos. 6,112,116, 6,272,379 and 6,609,023 describe systems and algorithms for detecting the onset of acute myocardial infarction and providing both treatment and alarming to the patient. In U.S. Patent Application No. 60/524,873, Fischell et al. describe a Guardian system for the long term tracking of myocardial ischemia to provide early prediction of coronary obstruction before the occurrence of a complete coronary artery blockage that results in an AMI.

Fischell et al., in the above references, describes a physician's programmer as a laptop computer like device designed to upload programming to the implant and download electrogram data collected by the implant. Although the parameters to be uploaded from the programmer are described by Fischell et al., the programmer functional screens using a graphical user interface (GUI) to simplify setting the parameters are not discussed. Also not described by Fischell et al. are techniques for display of the multiplicity of recorded electrogram and/or electrocardiogram segment data downloaded from the implant. Finally, Fischell et al. do not describe programmer displays associated with the collection, analysis and display of heart signal parameter histogram data captured over time by the implant.

Although often described as an electrocardiogram (ECG), the stored electrical signal from the heart as measured from electrodes within the body should be termed an "electrogram." The early detection of an acute myocardial infarction or exercise-induced myocardial ischemia caused by an increased heart rate or exertion is feasible using a system that can detect a change in a patient's electrogram. The portion of such a system that includes the means to detect a cardiac event is defined herein as a "cardiosaver," and the entire system including the cardiosaver and the external portions of the system is defined herein as a "Guardian system."

Furthermore, although the masculine pronouns "he" and "his" are used herein, it should be understood that the patient or the medical practitioner who treats the patient could be a man or a woman. Still further the term "medical practitioner" shall be used herein to mean any person who might be involved in the medical treatment of a patient. Such a medical practitioner would include, but is not limited to, a medical doctor (e.g., a general practice physician, an internist or a cardiologist), a medical technician, a paramedic, a nurse or an electrogram analyst.

The term "cardiac event" refers to any specific abnormal action of a patient's heart. ST shift related cardiac events and arrhythmias are cardiac events. ST shift related cardiac events include acute myocardial infarctions or ischemia caused by effort (such as exercise) and/or an elevated heart rate. The ST segment voltage change in ST shift related cardiac events may be either elevation (a positive voltage shift) or depression (a negative voltage shift). Arrhythmias include bradycardia, tachycardia or an arrhythmia such as atrial fibrillation, atrial flutter, ventricular fibrillation, and premature ventricular or atrial contractions (PVCs or PACs, respectively).

For the purpose of this invention, the term "electrocardiogram" is defined to be the heart's electrical signals sensed by one of more skin surface electrodes that are placed in a position to indicate the heart's electrical activity (depolarization and repolarization). An electrocardiogram segment refers to the recording of electrocardiogram data for either a specific length of time, such as 10 seconds, or a specific number of heart beats, such as 10 beats. For the purposes of this specification, the PQ segment of a patient's electrocardiogram is the typically flat segment of a beat of an electrocardiogram that occurs just before the R wave.

For the purpose of this invention, the term "electrogram" is defined to be the heart's electrical signals from one or more implanted electrode(s) that are placed in a position to indicate the heart's electrical activity (depolarization and repolarization). An electrogram segment refers to the recording of electrogram data for either a specific length of time, such as 10 seconds, or a specific number of heart beats, such as 10 beats. For the purposes of this specification, the PQ segment of a patient's electrogram is the typically flat sub-segment of an electrogram that occurs just before the R wave. The ST segment is the sub-segment of an electrogram that begins shortly after the R wave and ends just before the T wave (or it may include all or part of the T wave). A beat is defined as a sub-segment of an electrogram or electrocardiogram segment containing exactly one R wave. ST and PQ segments of a beat within an electrogram segment are defined herein as sub-segments of the electrogram segment. For the purposes of this specification, the terms "detection" and "identification" of a cardiac event have the same meaning.

Heart signal parameters are defined to be any measured or calculated value created during the processing of one or more beats of electrogram data. Heart signal parameters include PQ segment average value, ST segment voltage average value, R wave peak value, ST deviation, daily median ST deviation, daily mean ST deviation, ST shift, average signal strength, T wave peak height, T wave average value, T wave deviation, heart rate and R-R interval. ST segment voltage average value, ST deviation, daily median ST deviation, daily mean ST deviation, and ST shift are examples of ST segment related measurements.

SUMMARY OF THE INVENTION

The present invention is a physician's programmer designed to interface with an implanted medical device (a cardiosaver) designed to detect cardiac irregularities including arrhythmias, AMI and ischemia, as well as to capture diagnostic data on the patient's cardiovascular condition. The programmer features of the present invention are also applicable to programmers used with pacemakers or ICDs having the capability to detect cardiac irregularities. A cardiosaver or cardiosaver device is described by Fischell et al. in U.S. Pat. Nos. 6,112,116, 6,272,379 and 6,609,023 and U.S. Patent Application No. 60/524,873 incorporated herein by reference. For the purposes of this disclosure, the term "cardiosaver" will be used to include any of the features of the cardiosaver or cardiosaver described by Fischell et al.

Specifically, the present invention physician's programmer includes a graphical user interface (GUI) that facilitates setting of parameters for the detection of cardiac events and data recording. These parameters include event detection thresholds and timing parameters for excessive ST segment shift detection algorithms designed to detect AMI and ischemia. The GUI allows the physician to select any beat or series of beats from any displayed electrogram or ECG segment to be used as the sample for setting detection parameters. Furthermore, once selected, the values of specific parameters such as PQ and ST segment start and end times can be displayed graphically on other beats or electrogram segments.

An important aspect of the implant is the capability to automatically adjust the start time and duration of the ST and PQ segments used for the calculation of ST shifts. As the patient's heart rate changes during daily activities, the implant must adjust these time intervals for each beat in relation to the R-R interval for that beat. In other words, if the R-R interval shortens (higher heart rate), then the ST and PQ segments would move closer to the R wave peak and the segment durations would also become shorter. Specifically, the start time of the ST and PQ segments is defined as the time interval between the R wave and the start of the ST and PQ segments. The start time of the ST and PQ segments may be adjusted in linear proportion to the R-R interval, in proportion to the square root of the R-R interval, or by a look-up table created from previously collected patient electrograms. It is preferable to base these times on the R-R interval from the beat before the current beat to the current beat. As calculating the square root is a processor intensive calculation, the preferred implementation of this feature is to have the present invention programmer pre-calculate the values for the start time and duration of PQ and ST segments during programming. These values would then be uploaded to the implant where for each R-R interval or range of R-R intervals, the start times and/or durations for the segments are stored in a look-up table. Specifically, the present invention programmer plays an important part in this capability. The programmer allows the physician to select any beat from the multiplicity of electrogram segments and then adjust ST and PQ locations in time with respect to the R wave. The programmer allows the physician to adjust the ST and PQ locations graphically, by "dragging" bars overlaid on a beat that correspond to PQ and ST location start and end times. The programmer will then create the look-up table that specifies PQ and ST segment start and duration for a multiplicity of R-R interval values. In this way, the implant does not need to perform the significant amount of processing required to adjust the PQ and ST segment start and duration times.

The present invention programmer also includes the capability to specify detection parameters relative to cardiac arrhythmias such as a low heart rate limit below which bradycardia is detected, a high heart rate limit above which tachycardia is detected, and limits on R-R interval and R-R interval variability indicating the presence of other cardiac arrhythmias.

The present invention also includes specific user interface features to allow different sets of detection parameters to be programmed for different heart rate (or R-R interval) ranges.

The present invention also includes the features that enable the physician to download and display electrogram recordings from the implant and upload the patient-specific programming to the implant.

An important function of a cardiosaver device, a pacemaker, or an ICD with cardiosaver capabilities is the ability to alert the patient with an internal and/or external alarm signal when a cardiac event or irregularity is detected. An important feature of the present invention physician's programmer is the ability to specify the cardiosaver response to each type of detected cardiac event or irregularity. The responses include doing nothing, data recording only, and patient alerting with data recording. The patient alerting includes activation of an internal alarm signal and/or an external alarm signal. The internal alarm signal may be a vibration, sound or subcutaneous electrical tickle generated by the implanted cardiosaver. The external alarm signal may be a vibration, sound or visual alert from an external alarm device (EXD) that is carried by the patient. The implant communicates with the external alarm device using wireless radio-frequency (RF) signals. The EXD has also been described by Fischell et al. in U.S. Pat. Nos. 6,112,116, 6,272,379 and 6,609,023 as an external alarm system or an external alarm transceiver.

In a preferred embodiment of the present invention, there are two types of internal and/or external alarm signals: an "EMERGENCY" alarm signaling the detection of a major cardiac event (e.g. a heart attack) and the need for immediate medical attention, and a less critical "SEE DOCTOR" alert signaling the detection of a less serious, non life threatening condition such as exercise-induced ischemia. The SEE DOCTOR alert signal would be used to tell the patient that he is not in immediate danger but should arrange an appointment with his doctor in the near future. In addition to the signaling of less critical cardiac events, the SEE DOCTOR alert signal could also signal the patient when the cardiosaver battery is getting low. Although the preferred embodiment programmer allows the selection for each type of event of either of two types of patient alerting, it is envisioned that three or more types could be allowed.

As an example of two different alarm signal patterns, an EMERGENCY alarm would be applied with a pattern of three short pulses every 5 seconds after the detection of a major cardiac event, and the less critical SEE DOCTOR alert would be signaled with one longer pulse every 7 seconds.

Specifically, for each detectable event, the physician's programmer allows the physician to specify the pattern and intensity of the alarm signal (if any) to be activated for each type of detected event. The programmer also allows the selection of what patient data (if any) is saved for each type of detected event. Furthermore, the physician's programmer provides test means to allow the physician to demonstrate each alarm pattern to the patient, including the ability to interactively adjust the intensity of the alarm signal.

It is also envisioned that the internal and/or external alarm signals could use an escalating alert to prevent the patient from being startled at a time when it is very important that he remain calm. Escalating alerts are described by Fischell et al. in U.S. patent application Ser. No. 10/765,040 that is incorporated herein by reference. The programmer would play an important role in setting the signal parameters associated with such an escalating alert. For example, if the escalation is an amplitude increase over time, the programmer would allow setting of the initial amplitude of the alarm signal to that which is barely perceptible by the patient and the upper amplitude of the alarm signal to that which is extremely noticeable but does not cause discomfort.

An important aspect of the Guardian system is the ability to capture clinically relevant electrogram data for later physician review using the physician's programmer. The present invention programmer uses a GUI to interactively display selected subsets of the multiplicity of stored electrograms. The GUI also includes the capability to select any beat of any stored electrogram for use in interactively setting the various cardiac event detection parameters to be uploaded to the implant.

Furthermore, the present invention programmer has additional capability to analyze and display histograms and other statistical data collected by the implant and downloaded to the physician's programmer. This includes the capability to graphically display changes over time from multiple histogram downloads. The programmer GUI also includes the ability to show any or all of the following:

1. multiple histograms from a single time period;
2. combined histograms from multiple time periods; and
3. graphs displaying changes in stored histogram data over a multiplicity of time periods.

The present invention programmer also has the capability to command the implant to capture specific types of histogram data including the programming of time period and data ranges associated with each histogram. The programmer can also command the implant to clear the data (reset all bins to zero) in one or more of the cardiosaver histograms.

The present invention programmer also is designed to process downloaded histogram data to suggest and/or set detection parameters (AUTOPICK) for future cardiac event detection. For example, the cardiosaver histogram memory could be divided into sections having 5 histograms, where each of the five histograms corresponds to a different heart rate range and the bins (counters) within each histogram correspond to different levels of ST deviation. In this example, the patient would perform a stress test. During the stress test as the patient's heart rate increases, the five histograms will sequentially build up a representation of ST deviation for beats in each heart rate range. These histograms would then be downloaded to the programmer. The programmer might, for example, calculate the mean (or median) and standard deviation of the distributions in each histogram and use these data to AUTOPICK ST shift event threshold settings that would not initiate alarms at the ST shift levels seen during the stress test. Thus events would only be detected at ST shift levels significantly larger than those seen during the stress test. For example, the programmer could calculate the mean plus or minus 3 standard deviations as the positive and negative detection thresholds, respectively. If a stress test is not possible, the AUTOPICK function could analyze the last week's histograms of ST deviation for every beat processed by the cardiosaver to suggest thresholds for detection. The AUTOPICK function would also be of great value if the patient comes in with a false positive ST shift detection, as the AUTOPICK function will choose new thresholds that would have not triggered on the ST shifts that caused the false positive detection.

The present invention physician's programmer also includes security and reliability features. Ideally, one would like to use a commercially available laptop computer as the hardware platform for the physician's programmer. It is also extremely advantageous to be able to build the physician's programmer application on top of a Windows, LINUX or MAC operating system so as to take advantage of all of the software tools available. Unfortunately, using a full standard operating system, even one as reliable as Windows 2000, makes it difficult to safeguard the patient data and reduce the probability of failure. The FDA also prefers programmers that do not allow other applications (e.g. word processing), as these applications might affect the primary programmer application. The present invention physician's programmer includes specific techniques for hardening a laptop with a standard operating system to improve reliability and security.

These techniques include:
1. Using the BIOS password feature rather than a password built in to the operating system;
2. Removing all access and references to the base operating system so that the laptop boots to the physician's programmer application directly;
3. Requiring a secondary password to administer the physician's programmer and upgrade the software; and
4. Having a mirrored copy of the patient data including electrograms normally stored on the hard disk of the programmer (the primary storage means). The mirrored copy would typically be stored in non-volatile (e.g. flash) memory. This can be either a memory card such as a compact flash, SD, or memory stick, a microdrive or a USB (thumbdrive) flash memory device.

The implanted cardiosaver could have subcutaneous electrodes and/or electrodes located on a right ventricular or atrial pacemaker lead. It is also envisioned that one or more electrodes may be placed within the superior vena cava. One version of the implanted cardiosaver device using subcutaneous electrodes would have an electrode located under the skin on the patient's left side. This could be best located between 2 and 20 inches below the patient's left arm pit. The cardiosaver case that would act as the indifferent electrode would typically be implanted like a pacemaker under the skin on the left side of the patient's chest.

The physician's programmer would typically utilize the same RF interface to the implant as the external alarm device, the difference being that the programmer would have the ability to modify the programming of the implant while the external alarm device can only download data from the implant. The present invention programmer's RF interface is designed to operate at a distance of greater than 6 inches and as far away from the patient as 10 feet. The RF interface would typically include a long range telemetry chipset such as the CC1000 chipset from CHIPCOM. The RF interface used by the programmer could be the same external alarm device as is used by the patient or it might be a version of the external alarm device modified for connection to the programmer. The programmer RF interface could also include near field telemetry (similar to that used in pacemakers and ICDs) that would be used to initiate a communication session with an implanted cardiosaver. In this way, the implanted cardiosaver need not monitor for incoming long range telemetry which requires much more power than monitoring for incoming near field telemetry.

The programmer is designed to program the time interval for collection of baseline electrogram segments used by the implant's ST shift detection technique as described by Fischell et al. in U.S. Pat. No. 6,609,023. For example, the programmer could set the time interval for baseline data capture to as short as once every minute to as long as once per day. Also a feature of the programmer is the ability to set the baseline data comparison time interval, i.e. which baseline data (how far in the past) should be used for comparison against recently captured data. For example, if the baseline data collection time interval is one hour, the baseline data comparison time interval could be set with the programmer to be 6, 12, 24, or 48 hours. It is also envisioned that different baseline data collection and comparison time intervals could be applied by the programmer to different cardiac event detection algorithms. For example, Fischell et al. in U.S. Pat. No. 6,609,023 describe an ST shift detection algorithm with baseline data collection and comparison time intervals of 1 and 24±½ hours respectively and a T wave shift detection algorithm with baseline data collection and comparison time intervals of 1 minute and 5±½ minutes.

The processing of each of the baseline electrogram segments would typically involve calculating the average of one or more heart signal parameters over two or more beats of the baseline electrogram segment. It is envisioned that an additional programmer feature is the ability to specify the number of beats of a baseline electrogram segment that is processed by the implant to calculate the average of a heart signal parameter. For example the physician could use the programmer to command the implant to calculate the average ST deviation for the first 5 full beats of each baseline electrogram segment.

One such heart signal parameter is "ST deviation" where the ST deviation for a single beat of an electrogram segment is defined to be the difference between the average ST segment voltage and the average PQ segment voltage. The term ST shift is defined to be the difference between the ST deviation of a heart beat and a previously stored baseline average ST deviation.

Fischell et al. in U.S. Pat. No. 6,609,023 fully describe an example of how the ST and PQ segments are measured and averaged and how excessive ST shift is detected. The present invention programmer plays an important part in enabling the proper function of the excessive ST shift detection algorithms described by Fischell et al.

Another important feature of the cardiosaver is an event history log of every detection, response and data communication session. The event history log would also include the patient acknowledgement of an EMERGENCY Alarm or SEE DOCTOR alert by use of the alarm silence button on the external alarm device. The event log would typically be uploaded to the programmer along with electrogram datasets.

Although the descriptions of the present invention in most cases refer to the preferred embodiment of an implanted cardiosaver processing electrogram data from implanted electrodes, the techniques described are equally applicable to the alternate embodiment where the external cardiosaver processes electrocardiogram data from skin surface electrodes.

Thus an object of the present invention is to have a physician's programmer designed to facilitate setting and uploading to an implanted device, the parameters for an ST shift algorithm designed to detect ischemia and AMI.

Another object of the present invention is to have a physician's programmer designed to facilitate setting and uploading to an implanted device, alarm settings including pattern and intensity.

Another object of the present invention is to have a physician's programmer designed to interact with a cardiosaver to demonstrate one or more alarm patterns to the patient.

Yet another object of the present invention is to have a physician's programmer designed to interact with a cardiosaver to demonstrate one or more alarm signal intensities to the patient.

Yet another object of the present invention is to have a physician's programmer designed to interact with an implanted cardiosaver device to demonstrate either or both internal alarm signals or external alarm signals to the patient.

Another object of this invention is to have a physician's programmer designed to facilitate setting and uploading to an implanted device, the specific response of the implant to a detected cardiac event including settings for the alarm signals and event data recording.

Still another object of this invention is to have a physician's programmer designed to facilitate setting and uploading to an implanted device, the upper and lower limits of two or more heart rate ranges.

Still another object of this invention is to have a physician's programmer designed to facilitate setting and uploading to an implanted device, different detection parameters for two or more heart rate ranges.

Yet another object of the present invention is to have a physician's programmer designed to display a multiplicity of electrogram segments and upon selection of any beat of any electrogram segment, enable a graphical user interface display of the selected beat.

Yet another object of the present invention is to have a physician's programmer designed to use a graphical user interface display of a beat to interactively set specific cardiac event detection parameters.

Yet another object of the present invention is to have a physician's programmer designed to display a visual representation of the detection parameter settings on multiple beats of a displayed electrogram segment.

Yet another object of the present invention is to have the physician's programmer adapt the display of detection parameters to the R-R interval of each beat in the display.

Yet another object of the present invention is to have the physician's programmer upload data to an implanted cardiosaver to allow the cardiosaver to adapt its ST shift detection algorithms to beats having different R-R intervals.

Yet another object of the present invention is to have the physician's programmer built into a laptop PC where security is enhanced using the laptop BIOS password feature.

Yet another object of the present invention is to have the physician's programmer use a standard PC operating system where the PC boots directly to the physician's programmer software and access to normal operating system controls, features and applications are not allowed.

Yet another object of the present invention is to have the physician's programmer mirror patient data to a removable non-volatile data storage device.

Yet another object of the present invention is to have the physician's programmer create the look-up table for electrogram sub-segment timing as a function of R-R interval.

Yet another object of the present invention is to have the physician's programmer upload the look-up table to a cardiosaver.

Another object of the present invention is to have the programmer capable of displaying stored histograms downloaded from the cardiosaver.

Another object of the present invention is to have the programmer include the capability to set detection thresholds for cardiosaver histograms that will cause an alarm to be triggered when the threshold is exceeded.

Still another object of the present invention is to have a programmer that can calculate a moving average over relevant time periods of downloaded histogram data.

Yet another object of the present invention is to have a programmer that can display the combination of multiple histograms downloaded at different times.

Yet another object of the present invention is to have a programmer that can process downloaded data to AUTOPICK settings for cardiac event detection parameters including the thresholds for ST shift detections.

Yet another object of the present invention is to have a programmer that can manually clear one or more sections of histogram memory.

Yet another object of the present invention is to have a programmer that can display the event log used by the cardiosaver to capture the time and cause of every cardiac event and patient interaction.

These and other objects and advantages of this invention will become obvious to a person of ordinary skill in this art upon reading of the detailed description of this invention including the associated drawings as presented herein.

BRIEF DESCRIPTION OF THE DRAWINGS

FIG. 2 is the bios login screen of the physician's programmer.

FIG. 3 is the pop-up login screen of the physician's programmer.

FIG. 4 is an example of the main menu (patient information) screen for the present invention physician's programmer

DETAILED DESCRIPTION OF THE INVENTION

Figure 1:
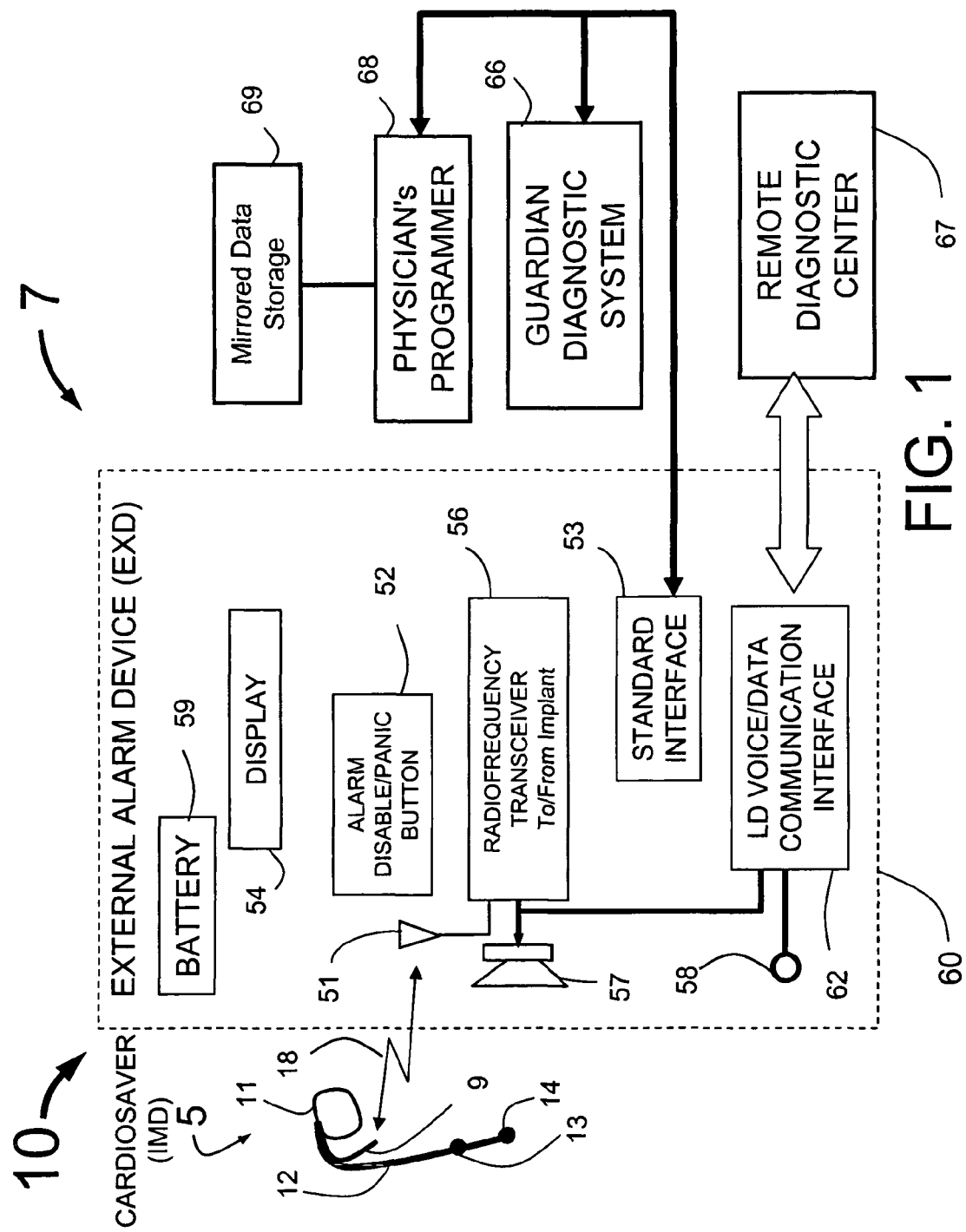
FIG. 1 illustrates a guardian system for the detection of cardiac irregularities and for warning the patient that a cardiac event is occurring.

FIG. 1 illustrates one embodiment of the guardian system 10 consisting of an implanted cardiosaver 5 and external equipment 7. The battery powered cardiosaver 5 contains electronic circuitry that can detect a cardiac event such as an acute myocardial infarction or arrhythmia and alert the patient when the event occurs. The cardiosaver 5 can store the patient's electrogram for later readout and can send wireless signals 18 to and from the external equipment 7. The functioning of the cardiosaver 5 is described fully in the incorporated Fischell et al. patents and patent applications referenced above. Throughout this section the cardiosaver 5 may also be identified as the implant, implanted device, Implanted Medical Device, or IMD.

The cardiosaver 5 has at least one lead 12 having multi-wire electrical conductors with surrounding insulation. The lead 12 is typically a standard bipolar pacemaker lead having two electrodes 13 and 14. The lead 12 could advantageously be placed through the patient's vascular system similar to the placement of a pacemaker lead, with the electrode 14 being placed into the apex of the right ventricle. The metal case 11 of the cardiosaver 5 could serve as an indifferent electrode with either or both electrodes 13 and/or 14 being active electrodes. It is also conceived that the electrodes 13 and 14 could be used as bipolar electrodes. Other lead placements are also possible including a subcutaneous placement where the electrode 14 is located under the skin on the patient's left side. The electrode 14 could be best located between 2 and 20 inches below the patient's left arm pit. The cardiosaver case 11 could act as the indifferent electrode and would typically be implanted under the skin on the left side of the patient's chest. The antenna 9 of the cardiosaver 5 provides the two-way wireless data communication 18 with the external equipment 7. The cardiosaver 5 might also include pacemaker or ICD circuitry as described by Fischell et al. in U.S. Pat. No. 6,112,116. The cardiosaver 5 also includes patient alerting means capable of generating an internal alarm signal in response to one or more detected cardiac events. The internal alarm signal is programmable as to intensity and alerting pattern, and two or more different patterns may be pre-set to correspond to different levels of severity of a detected cardiac event. The preferred embodiment of the cardiosaver 5 uses a vibratory internal alarm signal with two different patterns and the programmer is designed to provide test means to enable a medical practitioner to demonstrate the different alarm patterns and adjust the intensity of the internal alarm signal.

FIG. 1 also shows the external equipment 7 that consists of a physician's programmer 68 with mirrored data storage 69, an external alarm device 60, and a guardian diagnostic system 66. The external equipment 7 provides means to interact with the cardiosaver 5. These interactions include programming the cardiosaver 5, retrieving data collected by the cardiosaver 5, and handling alarms generated by the cardiosaver 5.

The external alarm device 60 (also referred to herein as the external device 60 or EXD) typically includes an antenna 51, an alarm disable/panic button 52, a standard data communications interface 53, a display 54, a radiofrequency transceiver 56, an alarm speaker 57, and a long distance voice/data communications interface 62 with microphone 58. The external alarm device 60 can communicate with equipment at a remote diagnostic center 67 by data communications using the interface 62. The interface 62 also provides wireless two-way voice communication between the patient and the remote diagnostic center 67.

The external alarm device 60 provides the patient with a hand-held device that can:
1. Provide an additional audio alarm signal that can wake the patient up if necessary and/or provide information about the alarm to a caregiver.
2. Provide an alarm disable button 52 to turn off both internal and external alarm signals. If no alarm is present and the button 52 is pressed by the patient, then it will act as a panic button and call out to the remote diagnostic center for help.
3. Display the type of alert on the display 54.
4. Act as a speakerphone to allow voice communication between the remote diagnostic center 67 and the patient.

The external alarm device (EXD) 60 can also be used as the transceiver to provide the data communication link between the cardiosaver 5 and the physician's programmer 68 or the Guardian diagnostic system 66. The EXD connects to the programmer 68 through a standard data interface such as a USB, firewire, serial RS-232 or parallel interface, or the EXD could be inserted into a laptop's PCMCIA card slot. It is also envisioned that a standard wireless transmission protocol such as Bluetooth, 802.11.a, b or g could also provide the interconnection instead of a wired interface.

An important feature of the cardiosaver 5 of FIG. 1 is an event history log of every detection, response and data communication session. The event history log would also include the patient acknowledgement of an EMERGENCY Alarm or SEE DOCTOR alert by use of the alarm silence button 52 on the external alarm device 60. The event log would typically be uploaded to the programmer along with electrogram datasets.

The physician's programmer 68 would typically utilize the same RF interface to the implant as the external alarm device 60. In fact the external device 60 could function as the radiofrequency transceiver for the programmer 68. The radiofrequency transceiver 56 includes long range telemetry capability designed to operate at a distance from the cardiosaver 5 of greater than 6 inches and as far away as 10 feet or more. The radiofrequency transceiver 56 would typically include a long range telemetry chipset such as the CC1000 chipset from CHIPCOM. The radiofrequency transceiver 56 could also be a dual mode transceiver that includes near field telemetry (similar to that used in pacemakers and ICDs) that would be used to initiate a communication session with the implanted cardiosaver 5. In this way, the implanted cardiosaver need not monitor for incoming long range telemetry which requires much more power than monitoring for incoming near field telemetry. Therefore an important aspect of the present invention programmer is to include a dual mode radiofrequency transceiver 56 having both long range and short range telemetry, the short range telemetry being used to initiate a long range telemetry data communication session. The initiation of a long range data communication session would first require that the external device 60 connected to the programmer be placed within 6 inches or less of the implanted cardiosaver 5. Once in position, a session could be established by having the programmer send a signal through the short range telemetry capability of the RF transceiver 56 to the cardiosaver 5 instructing the cardiosaver to initiate a long range data communication session. In an alternate embodiment, the button 52 could be depressed once the external device 60 is within 6" of the implanted cardiosaver 5 to initiate a long range data communication session.

A programmer system is the combination of the programmer 68 and external device 60 where the radiofrequency transceiver 56 provides the programmer 68 with the two-way data communication capability used to send and receive signals, commands and data to and from the implanted cardiosaver 5.

It is also envisioned that a programmer version of the external device 60 having only the radiofrequency interface capability (without the alarm functionality) might be used instead of the external alarm device 60 that is designed to be carried by the patient.

If a cardiac event is detected by the cardiosaver 5, an alarm message is sent by a wireless signal 18 to the external alarm device 60 via the antenna 51. When the alarm is received, an electrical alarm signal is sent to the loudspeaker 57 that will cause the loudspeaker to emit sounds to alert the patient that an event has occurred. Furthermore, the external alarm device 60 can, depending upon the nature of the wireless signal 18, send an outgoing data message to the remote diagnostic center 67. When the detection of an acute myocardial infarction is the cause of the alarm, the external alarm device 60 could automatically notify the remote diagnostic center 67 that a heart attack has occurred, and an ambulance could be summoned by the remote diagnostic center 67 to bring the patient to a hospital emergency room.

The data message sent to the remote diagnostic center could include any or all of the following information: (1) a specific patient is having an acute myocardial infarction or other cardiac event, (2) the patient's name, address and a brief medical history, (3) a map and/or directions to where the patient is located, (4) the patient's stored electrogram including baseline electrogram data and the specific electrogram segment that generated the alarm, (5) continuous real time electrogram data, and (6) a prescription written by the patient's personal physician as to the type and amount of drug to be administered to the patient in the event of a heart attack.

The purpose of the physician's programmer 68 shown in FIG. 1 is to set and/or change the operating parameters of the implantable cardiosaver 5 and to read out, process and display data stored in the memory of the cardiosaver 5, including stored electrogram segments. When a laptop computer is used as the physician's programmer 68, it would require connection to an external alarm device 60 that would act as a wireless transceiver for communicating with the cardiosaver 5. The laptop Graphical User Interface (GUI) would be used to provide guidance to the physician in communicating with the cardiosaver 5. A graphical user interface typically includes a visual display and one or more input devices, such as keyboards, mice, trackballs and/or touch-screens.

The programmer 68 of the present invention would also be designed to display statistical data collected by the cardiosaver 5, including histograms, over time periods as long as a year. The programmer 68 is typically connected to mirrored data storage 69 that is used to mirror the patient data including electrograms that are stored on the programmer hard disk (the primary storage unit). Examples of devices that could be used for the mirrored data storage 69 include either a fixed or removable data storage devices. Examples of devices that could be used as the storage 69 include a hard disk drive, a USB thumbdrive, a compact flash card, a memory stick, an SD card flash memory unit, a writable CD or DVD optical removable disk, or a Floppy, Zip or Jazz Drive removable magnetic disk. The purpose of the mirrored data storage 69 is to provide mirroring for the patient data and also to, in the case of a removable storage unit, provide a means to send the data to a remote location for archival purposes.

The guardian diagnostic system 66 is used to display data from the cardiosaver 5 to allow a medical practitioner to assess the patient's condition. The guardian diagnostic system 66 could be located in the emergency room and/or cath lab of a hospital to reduce the time required from patient arrival to proper treatment. One embodiment of the guardian diagnostic system 66 uses a tablet (or touch-screen) PC which could provide the display of information downloaded from the cardiosaver similar to that of the programmer but without the capability to change the cardiosaver programming. A second embodiment of the guardian diagnostic system 66 uses a PDA or pocket PC which would be much smaller than the tablet PC embodiment and could be available to the patient or a medical practitioner to display selected electrogram and alarm information for diagnostic purposes.

FIG. 2 is the BIOS login screen 205 of the physician's programmer 68 of FIG. 1. The purpose of a BIOS login is that it absolutely prevents access to the laptop files through booting to a floppy disk or CD. The user would enter his password following the prompt 206 to unlock the programmer and boot directly to the programmer software with the programmer login dialog box 210 of FIG. 3. The programmer login dialog box 210 requires a login 212 and password 214 that will enable the user to access specific features of the programmer 68. There would be two or more classifications of users. For example, three classifications might be enabled: administrators, programmers, and diagnostic users. The administrator group can add users and reclassify users, access any data stored on the programmer for any patient, and perform any function of the other two groups. The programmer group can use the programmer 68 to display downloaded data, modify the programming of the cardiosaver 5, and access patient records for the patient whose cardiosaver 5 is communicating with the programmer 68. The diagnostic user group would only be able to display data in the programmer 68 for the patient whose cardiosaver 5 is communicating with the programmer 68. A fourth maintenance user group might be used to update the software in the programmer 68 for feature enhancements or bug fixes.

The preferred embodiment of the programmer 68 security might disable the BIOS login and not require a login for the programmer and diagnostic user groups who can only access patient data for the patient they are with. If access to other patient data is required, an administrator login screen would be enabled. Even administrators could not install new software as that ability is limited to the maintenance user group.

FIG. 4 is an example of the main menu (patient information) screen 220 for the present invention physician's programmer 68. This screen would come up when the communication session with a cardiosaver 5 is established. The communication status is shown in section 224 on the screen 220 by the EXD cable status marker 226 and the IMD session status marker 227. EXD is an acronym for the external alarm device 60. The status marker 226 would be green and the text to the right of the status marker would be "connected" if the programmer 68 is connected properly to a functioning EXD. If the programmer 68 is not connected properly to a functioning EXD, the status marker 226 would be red and the text to the right of the status marker would be "not connected." IMD (Implanted Medical Device) is an acronym used by the programmer 68 for the cardiosaver implant 5. The marker 227 will be green and the text will be "connected" if there is an active communication session between the cardiosaver 5 and the programmer 68 through the external alarm device 60; if not, the marker 227 will be red and the text will be "not connected."

Section 225 of the screen 220 presents the current patient implant information including the patient's physician, the physician's phone number, the cardiosaver 5 serial number, the implant date and the implanting center. The Patient information section 222 shows the patient's name, birth date, sex, and ID number and includes the name selection box 223 and notes 221. The notes box 221 of the section 222 provides an area for additional information on the patient's medical history or condition. It is envisioned that other information such as address, phone number and insurance company could also be displayed in section 222. Only administrators (who have logged in using the programmer login dialog box 210) would also be able to use the name selection box 223 to look at other patients' data.

The electrogram data set section 230 of the screen 220 lists all current patient electrogram data sets that have been uploaded from the IMD. The entry in section 230 for each electrogram data set includes the session number 234, upload date and time 235, the alarm type 236 if any, the time when the data was collected by the IMD 237, the set number for the specific download 238, and the comments field 239. This example shows three electrogram data sets 231, 232 and 233 for the fictitious patient Angela Smith. The data set 231 is an upload of the current contents of IMD electrogram memory at the time of upload and therefore has an alarm type of "NONE" in the field 236. Every upload from the IMD will typically include a current contents data set of the most recently stored electrogram data in the implant. The data set 232 is listed as EMERG.—AMI indicating an Emergency alarm data set resulting from the detection of an AMI. The data set 233 is a See Doctor alert data set which would be saved by the IMD in the event of the detection of an event that is typically not life threatening.

The message 228 on the screen 220 displays a context-specific tip to the user. In this case the tip reminds the user to click the Retrieve Data button 244 to get the latest electrogram data from the IMD. Upon selection of the button 244, the programmer 68 will upload all of the currently stored data within the memory of the IMD 5 of FIG. 1. After a data set has been uploaded to the programmer 68, the archive data button 245 can be selected to mirror the data set to the backup storage unit 69. After selecting a dataset with the pointing device of the GUI, the buttons 229, 246, 247, 248 and 249 provide functions that can be performed on any data set selected by the user. The Event Log button 229 will display the event log that was downloaded along with the selected dataset. The View button 246 (or a double click with a mouse on a specific data set) will open a data set display screen whose characteristics depend on the type of alarm 236. The Delete button 247 will delete the selected data set from the programmer 68 but will not delete the data set from the backup storage unit 69. The Edit Comment button 248 will allow text entry within the Comments field 239. The Print Summary button 249 will print a summary report of all of the patient information shown in screen 220.

The menu bar 226 includes the menus labeled "Patient" 226a, "Logout" 226b, "Administration" 226c, "Implant" 226d and "Help" 226e. The Patient menu 226a would typically include the selections of NEW, SELECT and PRINT PATIENT RECORDS. NEW allows initialization of the programmer 68 database record for a new patient, SELECT allows authorized users to choose a patient database record to view (which also can be done with the Name box 223), and PRINT PATIENT RECORDS will perform the same function as the Print Summary button 249. The Logout menu 226b would allow the choices of log the current user off and bring back the user login screen 210 of FIG. 3 or shut down the programmer. The Administration menu 226c would allow administrators to add authorized users, backup and restore the system, and set or change authorization levels for users of the programmer 68. Members of the programmer and diagnostic user groups could use the Administration menus to backup the system and change their passwords. The Implant menu 226d is used to program the IMD 5 of FIG. 1. It includes Initial Setup (see FIG. 16) used for the first time the IMD 5 is turned on before implant, and Initial Programming (see FIG. 17) used following implantation to initialize internal alarm signal intensity levels for the EMERGENCY alarm and SEE DOCTOR alert, testing the settings with the patient, and training the patient to recognize the two different signals.

The Implant menu 226d would also allow changes to the initial setup and initial programming to be made at a later time. The Help menu 226e would provide a built in instruction manual for use of the programmer 68. It is also envisioned that similar to many windows programs, the F1 function button when depressed would provide access to context-specific instructions at any time or on any screen.

The tablet PC embodiment of the guardian diagnostic system 66 of FIG. 1 could also use the screen 220 in accessing patient information stored in the IMD 5. The main differences between the screen 220 of the programmer 68 and the guardian diagnostic system 66 would be:

1. only the current patient record would be viewable as only the diagnostic user group is enabled on the guardian diagnostic system;
2. the logout menu 226b would be replaced by a shutdown menu as the guardian diagnostic system would not require the logins of either FIG. 2 or 3;
3. the Administration menu 226c would be disabled; and
4. the Implant menu 226d would be disabled.

Figure 5:
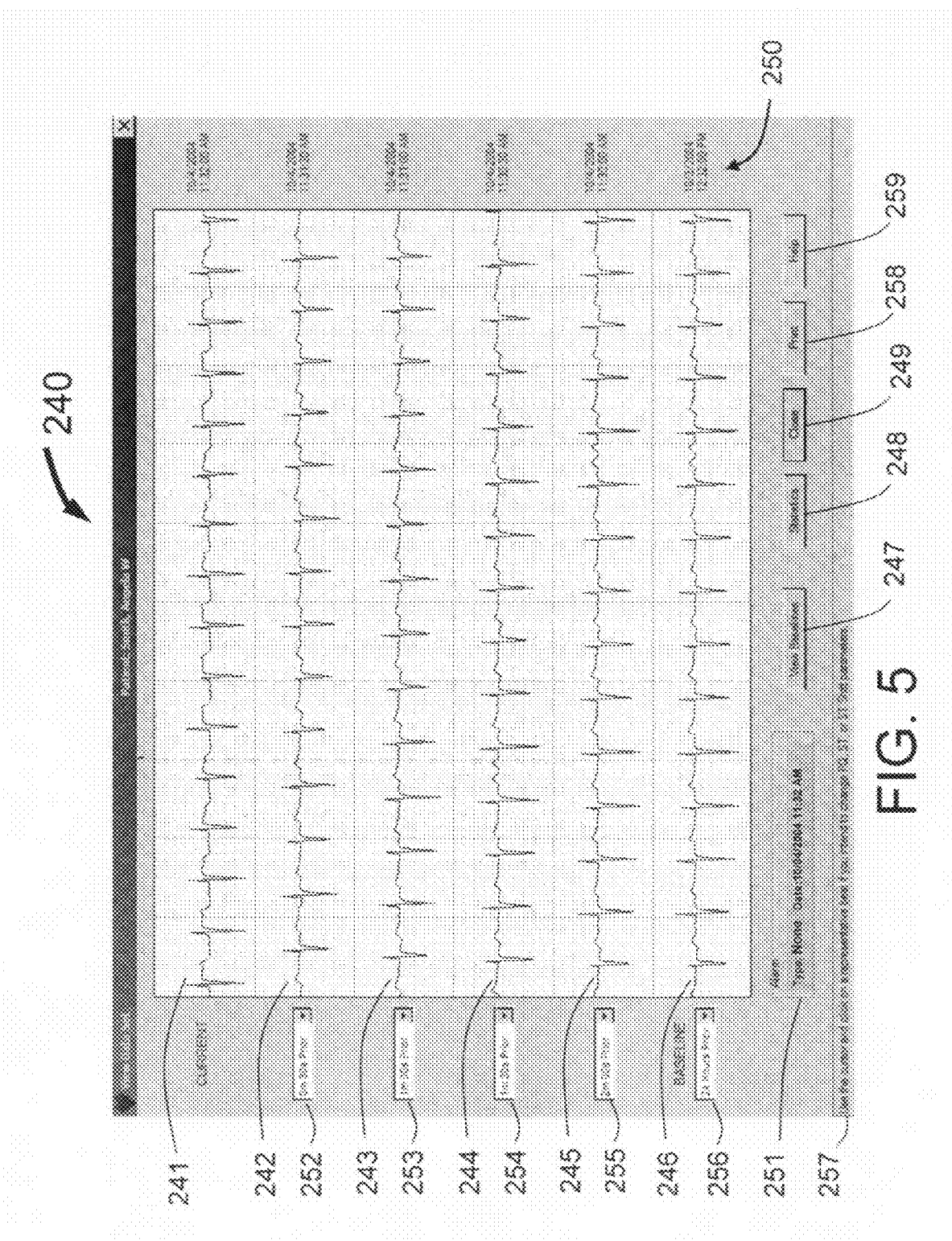
FIG. 5 is an example of the physician's programmer main display of the most recent electrogram segments in memory of the cardiosaver at the time of information upload.

FIG. 5 is an example of the physician's programmer View Data Set display screen 240 which displays the current contents data set 231 from the patient information screen 220 of FIG. 4. The section 251 shows the date and time of the data set 231 that was uploaded to the programmer 68 of FIG. 1. The Alarm Type of None indicates that there was no cardiac event associated with the electrogram data of the screen 240. The data set 240 is an example of a current contents data set 231 of FIG. 4 which includes the electrogram segments in memory of the IMD 5 of FIG. 1 at the time of uploading of stored data by the programmer 68 from the IMD 5.

The screen 240 shows 6 simultaneous electrogram segments 241 through 246 including the "current" electrogram segment 241 which is the most recent electrogram segment stored by the IMD 5 of FIG. 1 at the time of uploading the data to the programmer 68. Segment 242, 243, 244 and 245 are the display of four of the other most recent stored electrograms uploaded from the IMD 5 in the current data set 231. The selection boxes 252, 253, 254 and 255 provide the user the ability to select for display recently stored electrogram segments other than the last 4 segments saved by the IMD 5 before the current segment 241. The box 252 indicates that the electrogram segment 242 was 30 seconds prior to the current segment 241. Similarly the boxes 253, 254 and 255 indicate the segments 243, 244 and 245 were recorded 1 minute, 1 min. 30 sec., and 2 minutes respectively before the current segment 241. Although this example shows a 30 second recording interval between recently collected electrogram segments in the data set 231 of FIG. 4, the time between recordings could be either shorter or longer than 30 seconds. Although the IMD 5 might record electrogram segments every 30 seconds, the most recent electrogram segments uploaded to the programmer might be a selection of those segments where the time between the uploaded segments would vary. For example, the most recent four uploaded segments might be at 30 second intervals, the prior four uploaded segments at one minute intervals and the prior four to those at 5 minute intervals.

Fischell et al. in U.S. Pat. No. 6,609,023 describe how the IMD 5 periodically records and processes baseline electrogram segments for use in detecting cardiac events. For example, the baseline segments might be collected once per hour, and the detection of a cardiac event would be based on a comparison of the most recently collected electrogram segment with the baseline segment from approximately 24 hours prior. The baseline electrogram segment display 246 with selection box 256 shows one of the baseline electrogram segments stored in the IMD 5 memory at the time of the data set 231 upload. The selection box 256 used to choose the specific baseline segment to be displayed shows here that baseline segment 246 was recorded approximately 24 hours prior to the current segment 241. The date and time field 250 displays the date and time that each of the electrogram segments 241 through 246 was recorded by the IMD 5 of FIG. 1.

Figure 6:
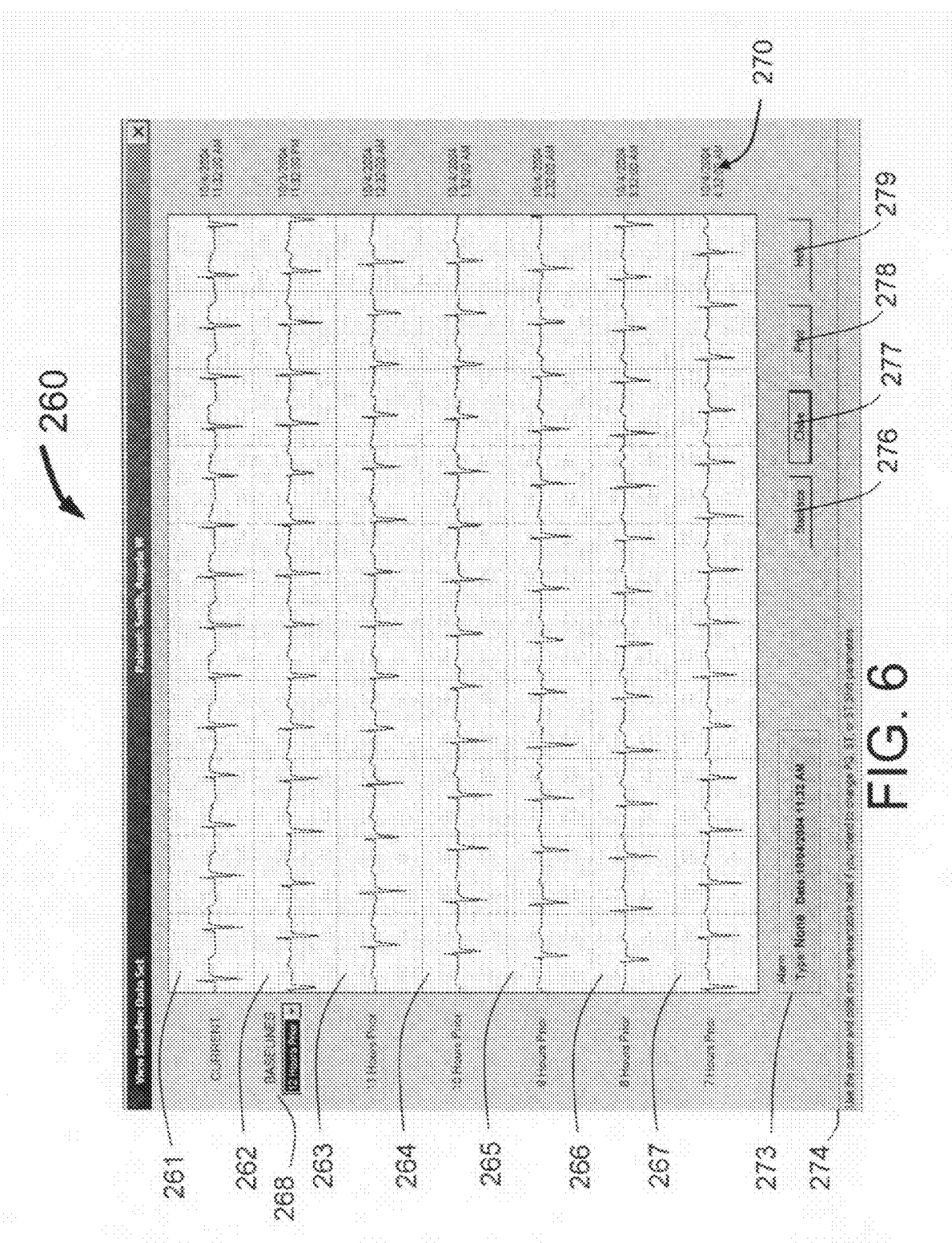
FIG. 6 is an example of the physician's programmer display of the baseline electrogram segments in memory of the cardiosaver at the time of information upload.

The View Baselines button 247 of FIG. 5 will activate the display of the View Baseline Data Set screen 260 of FIG. 6. The Statistics button 248 will activate the display of the Statistical Data Screen 400 of FIG. 15. The Close button 249 (or the X button in the upper right of the screen 240) will return to the main menu patient data screen 220 of FIG. 4. The Help button 259 provides access to instructions related to the current data set screen 240, as well as access to the entire built in instruction manual similar to the Help menu 226e of FIG. 4.

The Print button 258 will allow the user to select the printing of any of the following:
1. only the data shown on the current screen 240;
2. all the electrogram segments stored in the current data set 231 of FIG. 4; or
3. all of the data uploaded to the programmer 68 at the time of the upload of the current data set 231.

The tip field 257 provides a tip for use of the current data set screen 240. Here the tip field 257 states "Use the cursor and click on a representative beat if you intend to change PQ, ST or ST shift parameters". The programmer 68 graphical user interface is designed so that clicking the mouse or pointing device button with the cursor positioned over any beat of the displayed electrogram segments 241 through 246 will select that beat and access the Edit Implant Parameters screen 330 of FIG. 10 which will display the selected beat in an enlarged format and enable the editing of various implant parameters.

The screen 240 could also be used by the tablet PC embodiment of the guardian diagnostic system 66 of FIG. 1 to display electrogram data just uploaded from the IMD 5 when a patient arrives at an emergency room, cath lab or other location having the guardian diagnostic system 66. The only differences between the screen 240 of the guardian diagnostic system 66 and the programmer 68 would be the tip field 257, which would not be present in the diagnostic system, and the ability to click on a beat of one of the electrogram segments 241 through 246 to edit programming parameters for the detection of cardiac events by the IMD 5 of FIG. 1.

FIG. 6 is an example of the View Baseline Data Set screen 260 which shows the current electrogram segment 261, which is the same as the segment 241 of FIG. 5, and six of the baseline electrogram segments in the memory of the IMD 5 at the time of data upload of the data set 231 of FIG. 4. The selection box 268 can select one of the baseline electrogram segments of the data set 231 and that segment will be displayed as electrogram segment 262. The prior 5 electrogram segments to the segment 262 will be displayed as electrogram segments 263 through 267.

The date and time field 270 displays the date and time that each of the electrogram segments 261 through 267 were recorded by the IMD 5 of FIG. 1.

Figure 15:
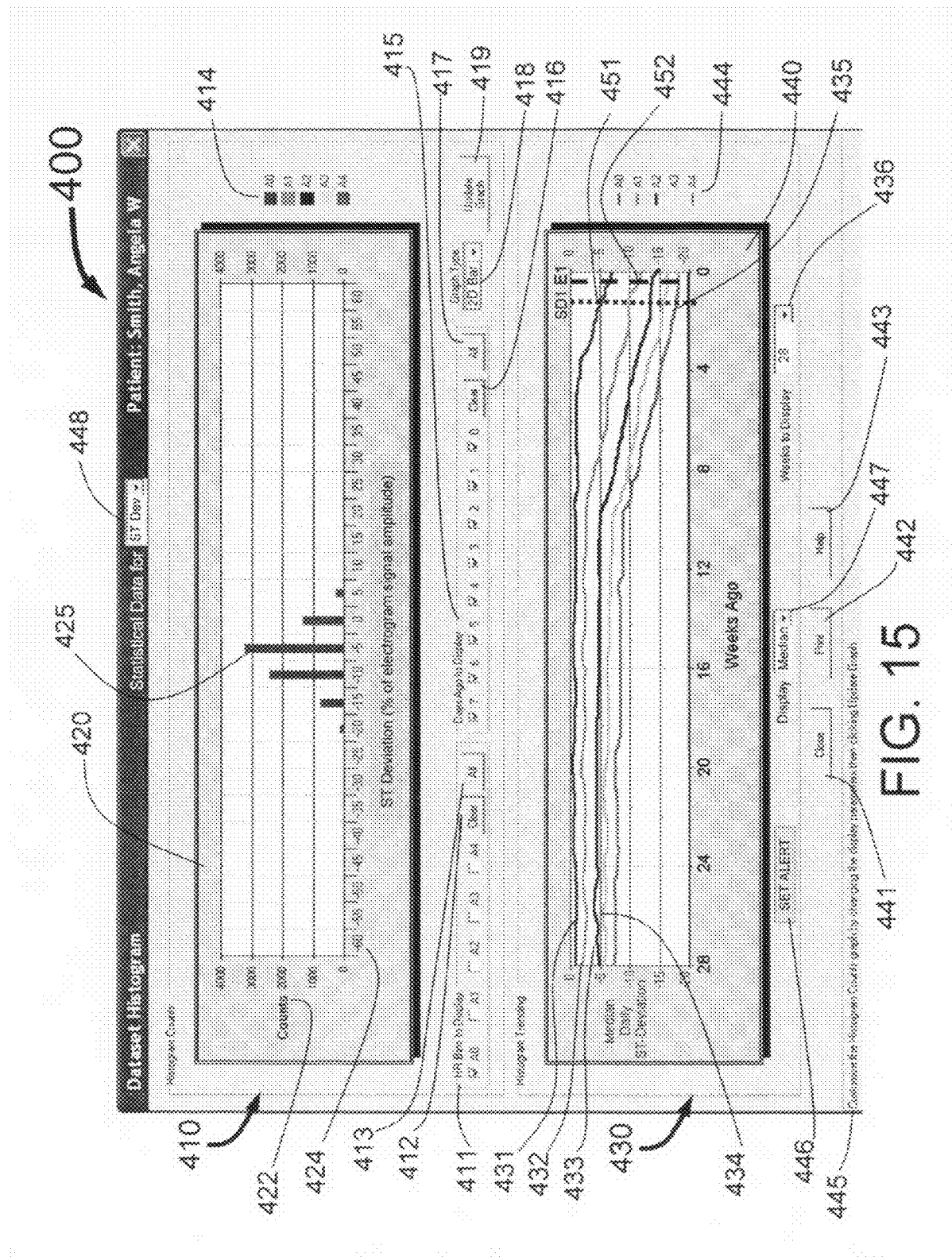
FIG. 15 is an example of the physician's programmer screen presenting statistical data including histograms of ST deviation.

The Statistics button 276 will activate the display of the Statistical Data Screen 400 of FIG. 15. The Close button 277 (or the X button in the upper right of the screen 260) will return to the View Data Set screen 240 of FIG. 5. The Help button 279 provides access to instructions related to the View Baseline Data Set screen 260, as well as access to the entire built in instruction manual similar to the Help menu 226e of FIG. 4.

The Print button 278 will allow the user to select the printing of any of the following:
1. only the data shown on the current screen 260;
2. all the electrogram segments stored in the current data set 231 of FIG. 4; or
3. all of the data uploaded to the programmer 68 at the time of the upload of the current data set 231.

The tip field 274 provides a tip for use of the View Baseline Data Set screen 260. Here the tip field 274 states "Use the cursor and click on a representative beat if you need to change PQ, ST or ST shift parameters". The programmer 68 graphical user interface is designed so that clicking the cursor on any beat of the 7 displayed electrogram segments 261 through 267 will access the Edit Implant Parameters screen 330 of FIG. 10.

The screen 260 could also be used by the tablet PC embodiment of the guardian diagnostic system 66 of FIG. 1 to display electrogram data just uploaded from the IMD 5 when a patient arrives at an emergency room, cath lab or other location having the guardian diagnostic system 66. The only differences between the screen 260 of the guardian diagnostic system 66 and the programmer 68 would be the tip field 274, which would not be present in the diagnostic system, and the ability to click on a beat of one of the electrogram segments 261 through 267 to edit programming parameters for the detection of cardiac events by the IMD 5 of FIG. 1.

Figure 7:
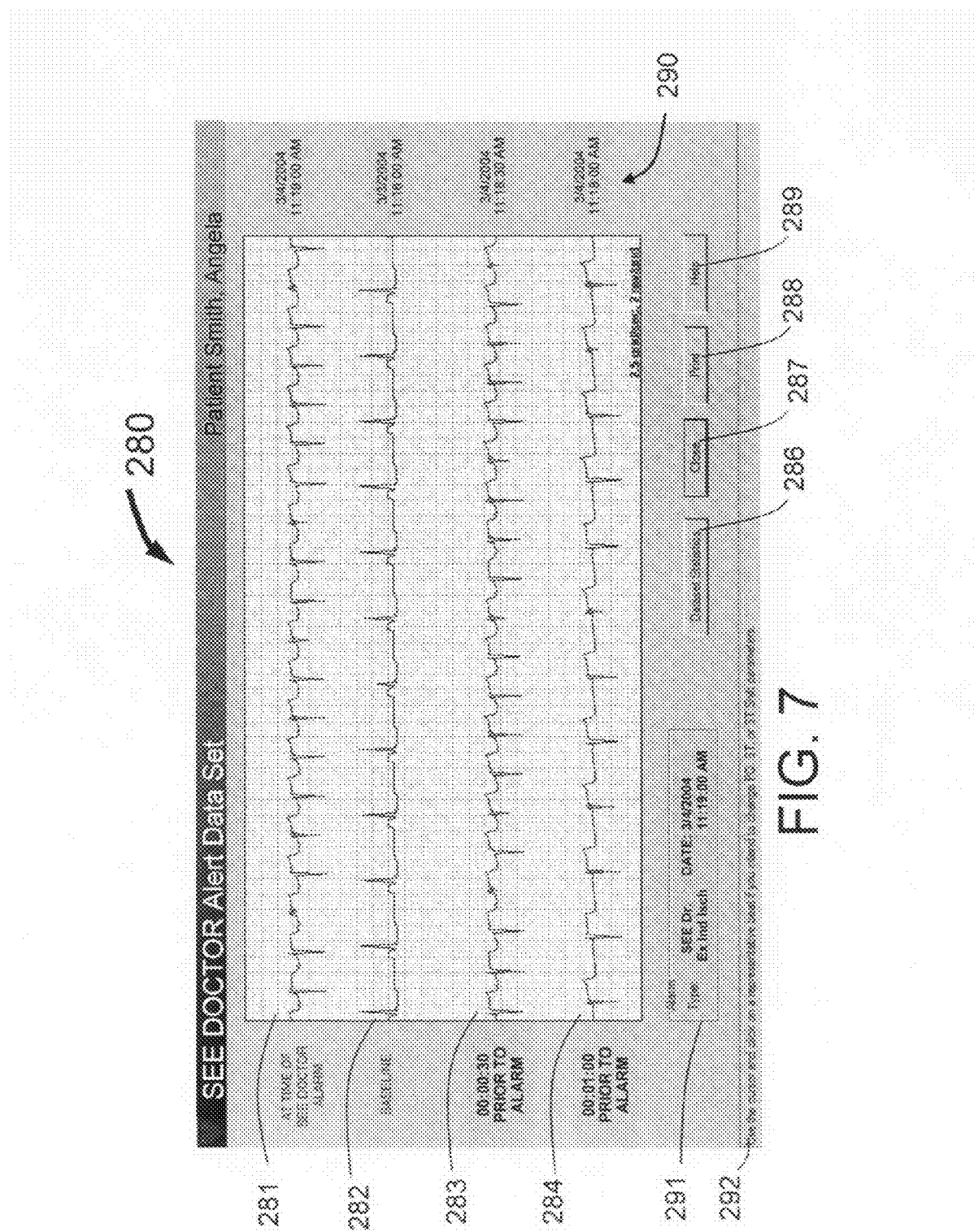
FIG. 7 is an example of the physician's programmer display of the electrogram segments for a SEE DOCTOR alert.

FIG. 7 is an example of the SEE DOCTOR Alert Data Set screen 280 that displays the SEE DOCTOR alert data set 233 selected from the patient data screen 220 of FIG. 4. The SEE DOCTOR alert data set screen 280 shows the electrogram segments 281 through 284. The electrogram segment 281 is the electrogram segment whose analysis by the IMD 5 of FIG. 1 identified the cardiac event that initiated the SEE DOCTOR alert. The electrogram segment 282 is the baseline electrogram segment that was used by the IMD 5 for comparison with the electrogram segment 281 to detect the cardiac event that initiated the SEE DOCTOR alert.

The electrogram segments 283 and 284 are the two electrogram segments preceding electrogram segment 281. Fischell et al. in U.S. Pat. No. 6,609,023 describe cardiac event detection algorithms where a cardiac event is identified when three consecutive electrogram segments test positively for the indicated cardiac event. The segments 281, 283 and 284 shown in screen 280 would be those three consecutive electrogram segments. The field 290 shows the time and date of each of the electrogram segments 281 through 284. The section 291 shows the date and time of the SEE DOCTOR alert as well as the Alarm Type being "SEE. Dr. Ex Ind Isch" meaning exercise-induced ischemia.

The Dataset Statistics button 286 will activate the display of the Statistical Data Screen 400 of FIG. 15. The Close button 287 will return to the patient data screen 220 of FIG. 4. The Help button 289 provides access to instructions related to the SEE DOCTOR Alert Data Set screen 280, as well as access to the entire built in instruction manual similar to the Help menu 226e of FIG. 4.

The Print button 288 will allow the user to select the printing of any of the following:
1. only the data shown on the current screen 280,
2. all the electrogram segments stored in the current data set 233 of FIG. 4, or
3. all of the data uploaded to the programmer 68 at the time of the upload of the SEE DOCTOR alert data set 233.

The tip field 292 provides a tip for use of the current data set screen 280. Here the tip field 292 states "Use the cursor and click on a representative beat if you intend to change PQ, ST or ST shift parameters". The programmer 68 graphical user interface is designed so that clicking the cursor on any beat of the 4 displayed electrogram segments 281 through 284 will access the Edit Implant Parameters screen 330 of FIG. 10.

The screen 280 could also be used by the tablet PC embodiment of the guardian diagnostic system 66 of FIG. 1 to display electrogram data just uploaded from the IMD 5 when a patient arrives at an emergency room, cath lab or other location having the guardian diagnostic system 66. The only differences between the screen 280 of the guardian diagnostic system 66 and the programmer 68 would be the tip field 292, which would not be present in the diagnostic system, and the ability to click on a beat of one of the electrogram segments 281 through 284 to edit programming parameters for the detection of cardiac events by the IMD 5 of FIG. 1.

Figure 8:
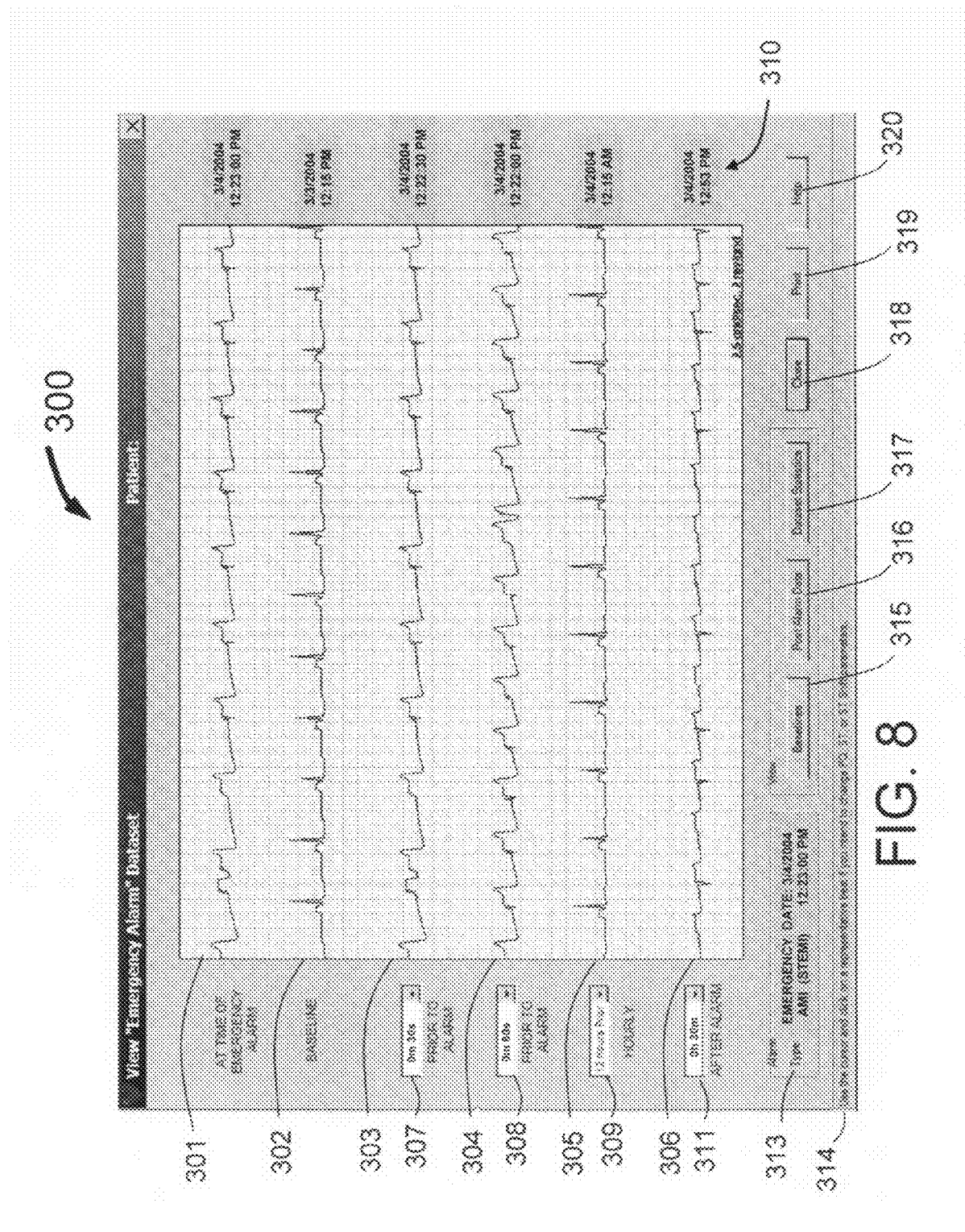
FIG. 8 is an example of the physician's programmer display of the electrogram segments for an EMERGENCY alarm.

FIG. 8 is an example of the View Emergency Alarm Dataset screen 300 which displays the AMI alarm data set 232 from the main menu screen 220 of FIG. 4. The section 313 shows the date and time of the EMERGENCY Alarm. The Alarm Type of EMERGENCY—AMI (STEMI) indicates that there was an ST elevation acute myocardial infarction detected by the IMD 5 of FIG. 1.

The screen 300 shows 6 simultaneous electrogram segments 301 through 306 including the "AT THE TIME OF EMERGENCY ALARM" electrogram segment 301 which is the electrogram segment whose analysis by the IMD 5 of FIG. 1 identified the AMI cardiac event. The electrogram segment 302 is the baseline electrogram segment that was used by the IMD 5 for comparison with the electrogram segment 301 to detect the cardiac event that initiated the EMERGENCY alarm.

The electrogram segments 303 and 304 are the two electrogram segments preceding electrogram segment 301 by 30 seconds and 1 minute respectively. Fischell et al. in U.S. Pat. No. 6,609,023 describe cardiac event detection algorithms where a cardiac event is identified when three consecutive electrogram segments test positively for the indicated cardiac event. The segments 301, 303 and 304 shown in screen 300 would be those three consecutive electrogram segments. The selection boxes 307 and 308 are used to select the display of other electrogram segments from the period just before the detection of the AMI that were recorded by the IMD 5 of FIG. 1 and saved for later physician review following the cardiac event detection.

The baseline electrogram segment display 305 with selection box 309 is the display of the baseline electrogram segment recorded by the IMD 5 approximately 12 hours before the detected cardiac event. The selection box 309 is used to choose the specific baseline segment to be displayed. The AFTER ALARM electrogram segment 306 with selection box 311 is the display of the electrogram segment that was recorded by the IMD 5 thirty minutes following the detection of the cardiac event. The selection box 311 is used to select the specific post-event electrogram segments from those that were recorded by the IMD 5 following the detection of the cardiac event.

The date and time field 310 displays the date and time that each of the electrogram segments 301 through 306 were recorded by the IMD 5 of FIG. 1.

The Baselines button 315 will activate the display of the View Baseline Data Set screen 260 of FIG. 6. The Post Alarm Data button 316 will activate the View Post Alarm Dataset screen 400 of FIG. 9. The Dataset Statistics button 317 will activate the display of the Statistical Data Screen 400 of FIG. 15. The Close button 318 (or the X button in the upper right of the screen 300) will return to the main menu patient data screen 220 of FIG. 4. The Help button 320 provides access to instructions related to the screen 300, as well as access to the entire built in instruction manual similar to the Help menu 226e of FIG. 4.

The Print button 319 will allow the user to select the printing of any of the following:
 1. only the data shown on the current screen 300;
 2. all the electrogram segments stored in the EMERGENCY—AMI data set 232 of FIG. 4; or
 3. all of the data uploaded to the programmer 68 at the time of the upload of the EMERGENCY—AMI dataset 232.

The tip field 314 provides a tip for use of the View EMERGENCY Alarm Data Set screen 300. Here the tip field 314 states "Use the cursor and click on a representative beat if you intend to change PQ, ST or ST shift parameters". The programmer 68 graphical user interface is designed so that clicking the cursor on any beat of the 6 displayed electrogram segments 301 through 306 will access the Edit Implant Parameters screen 330 of FIG. 10.

The screen 300 could also be used by the tablet PC embodiment of the guardian diagnostic system 66 of FIG. 1 to display electrogram data just uploaded from the IMD 5 when a patient arrives at an emergency room, cath lab or other location having the guardian diagnostic system 66. The only differences between the screen 300 of the guardian diagnostic system 66 and the programmer 68 would be the tip field 314, which would not be present in the diagnostic system, and the ability to click on a beat of one of the electrogram segments 301 through 306 to edit programming parameters for the detection of cardiac events by the IMD 5 of FIG. 1.

Figure 9:
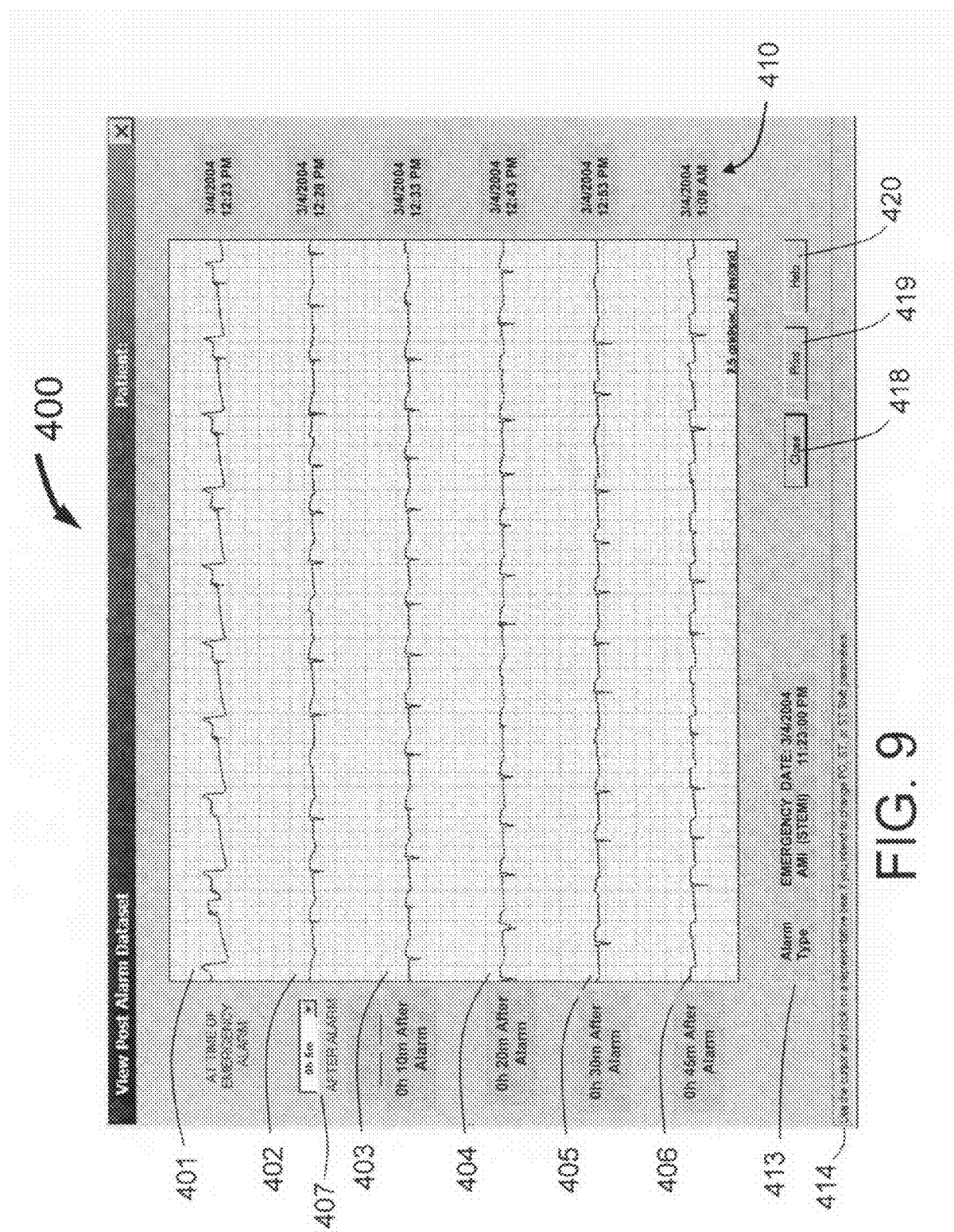
FIG. 9 is an example of the physician's programmer display of the post-event electrogram segments following an EMERGENCY alarm.

FIG. 9 is an example of the physician's programmer View Post Alarm Dataset screen 400 which is accessed by selecting the Post Alarm Data button 316 of the screen 300 of FIG. 8. The section 413 shows the same information as the section 313 of the screen 300 of FIG. 8 which is the date and time of the AT TIME OF EMERGENCY ALARM electrogram segment 401. The Alarm Type of EMERGENCY—AMI (STEMI) indicates that there was an ST elevation acute myocardial infarction detected by the IMD 5 of FIG. 1.

The screen 400 displays the electrogram segment 401 which initiated the detection of the EMERGENCY alarm cardiac event where segment 401 is the same as segment 301 of FIG. 8. Electrogram segments 402 through 406 represent 5 successive post-alarm electrogram segments recorded by the IMD 5 of FIG. 1. The selection box 407 is used to choose the first of the 5 successive post-alarm electrogram segments to be displayed on the screen 400. In this example, the selection box 407 has been used to select the segment 402 that was recorded 5 minutes after the alarm. The screen 400 shows here that the next four segments 403, 404, 405 and 406 were recorded 10, 20, 30 and 45 minutes, respectively, after the alarm. If selection box 407 is used to select a different post-alarm electrogram segment 402, then the next four segments 403, 404, 405, and 406 will also change.

The recording date and time for each of the electrogram segments 401 through 406 is shown in the field 410 on the right side of the screen 400.

The Close button 418 (or the X button in the upper right of the screen 400) will return to the View Emergency Alarm Dataset screen 300 of FIG. 8. The Help button 420 provides access to instructions related to the screen 400, as well as access to the entire built in instruction manual similar to the Help menu 226e of FIG. 4.

The Print button 419 will allow the user to select the printing of any of the following:
 1. only the data shown on the current screen 400;
 2. all the electrogram segments stored in the EMERGENCY—AMI data set 232 of FIG. 4; or
 3. all of the data uploaded to the programmer 68 at the time of the upload of the EMERGENCY—AMI dataset 232.

The tip field 414 provides a tip for use of the current data set screen 400. Here the tip field 414 states "Use the cursor and click on a representative beat if you intend to change PQ, ST or ST shift parameters". The programmer 68 graphical user interface is designed so that clicking the cursor on any beat of the 6 displayed electrogram segments 401 through 406 will access the Edit Implant Parameters screen 330 of FIG. 10.

The screen 400 could also be used by the tablet PC embodiment of the guardian diagnostic system 66 of FIG. 1 to display electrogram data just uploaded from the IMD 5 when a patient arrives at an emergency room, cath lab or other location having the guardian diagnostic system 66. The only differences between the screen 400 of the guardian diagnostic system 66 and the programmer 68 would be the tip field 414, which would not be present in the diagnostic system, and the ability to click on a beat of one of the electrogram segments 401 through 406 to edit programming parameters for the detection of cardiac events by the IMD 5 of FIG. 1.

Figure 10:
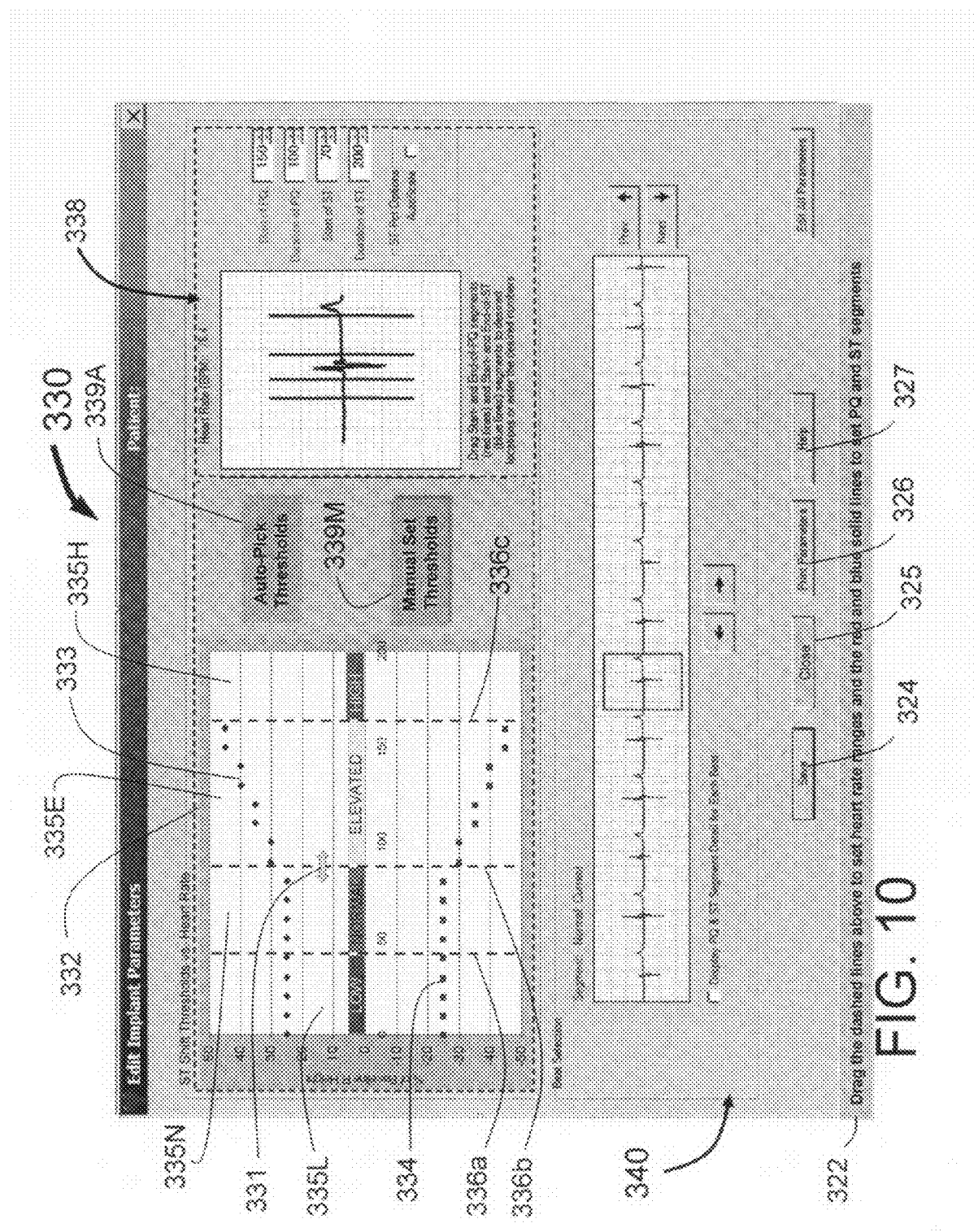
FIG. 10 is an example of the edit implant parameters screen used to select AUTOPICK or Manual Pick for the key parameters used by the Fischell et al. ST shift algorithm of U.S. Pat. No. 6,609,023.

FIG. 10 is an example of the Edit Implant Parameters screen 330 used to AUTOPICK the key parameters used by the ST shift algorithm described by Fischell et al. in U.S. Pat. No. 6,609,023. The section 332 of the Edit Implant Parameters screen 330 shows the currently programmed excessive ST shift positive and negative shift thresholds 333 and 334, as well as the Low, Normal, Elevated and High heart rate ranges 335L, 335N, 335E and 335H, respectively. The heart rate ranges 335L, 335N, 335E and 335H are adjusted with the programmer graphical user interface by placing the cursor 331 over one of the range adjustment lines 336a, 336b or 336c and dragging the line to the right or the left. The positive and negative shift thresholds 333 and 334 appear flat in the low and normal ranges 335L and 335 N but have a step function appearance in the elevated range 335E. This is because the elevated range 335E has 4 sub-ranges in which different excessive ST shift thresholds may be set as described by Fischell et al.

Figure 11:
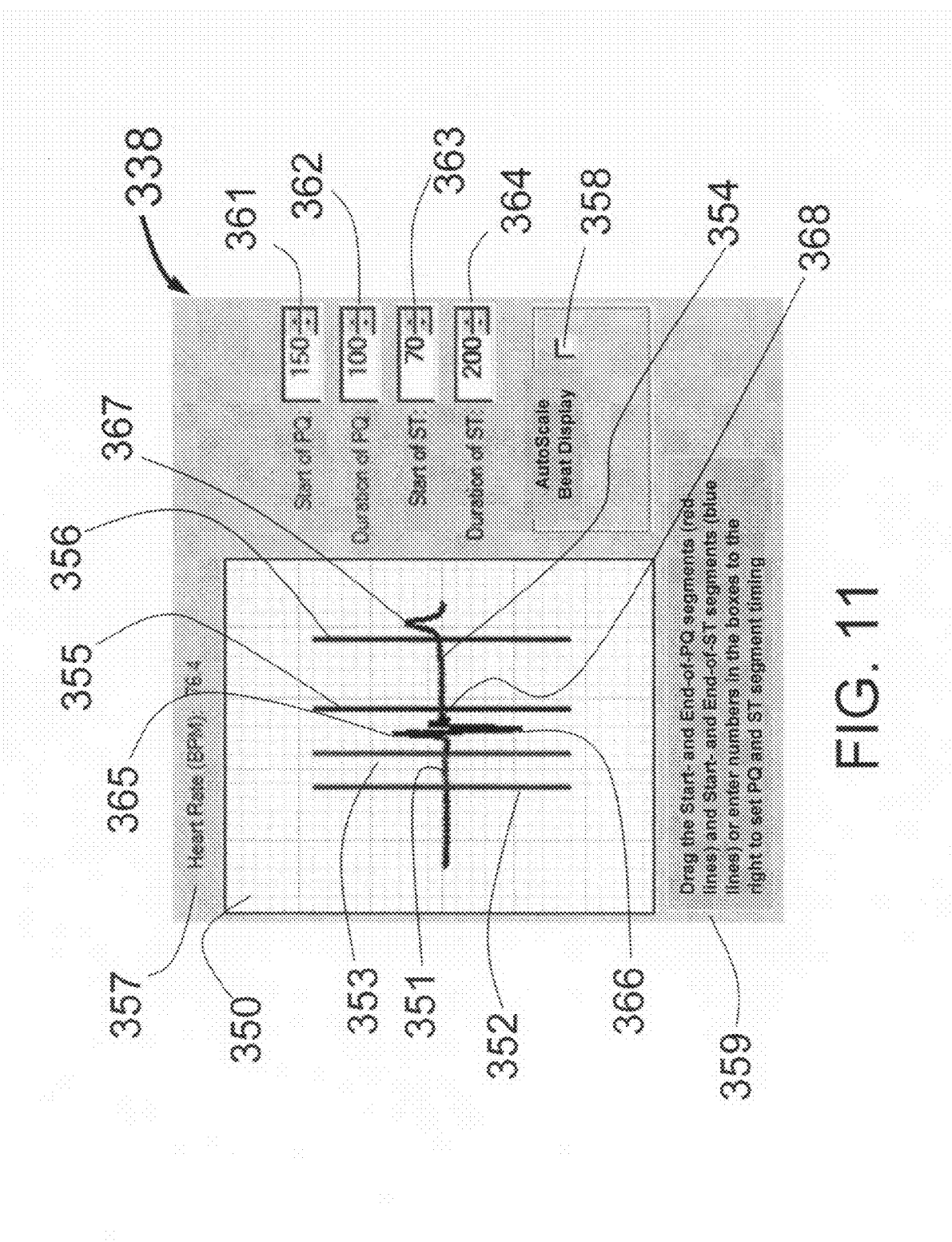
FIG. 11 is an enlargement of the PQ and ST segment parameter graphical user interface menu.

Once the heart rate ranges 335L, 335N, 335E and 335H are set (or left at the default setting for the programmer 68) the section 338 of the screen 330 is used to set the PQ and ST segment start time and durations as shown in detail in FIG. 11. The PQ and ST segment settings can be tested using the PQ-ST segment test section 340 of screen 330 which is shown in detail in FIG. 12.

Once the PQ and ST segment start times and durations are set (or the default settings of the programmer 68 are used), the excessive ST shift thresholds can either be set automatically by selecting the Auto-Pick Thresholds button 339A or the Manual Set Thresholds button 339M. The Auto-Pick Thresholds button 339A will initiate the automatic threshold selection process within the programmer 68. This process will analyze the data uploaded from the IMD 5 of FIG. 1 to calculate thresholds in each heart rate range that are high enough so that excessive ST shift is not detected in any electrogram segment of the data uploaded from the IMD 5.

Figure 12:
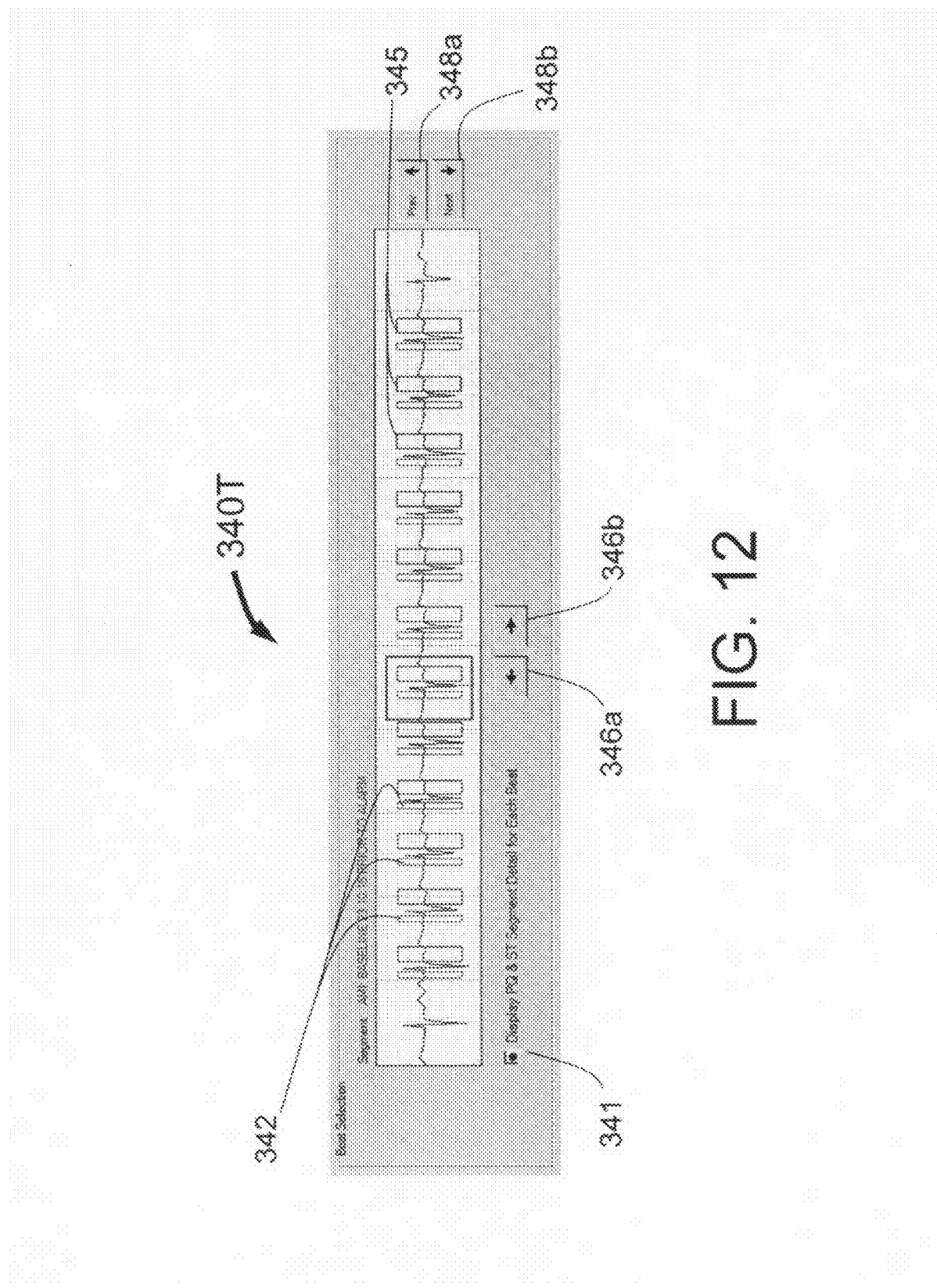
FIG. 12 is an enlargement of the PQ-ST segment test section of screen showing use of the test function that highlights the PQ and ST segments for each beat.

The tip field 322 provides a tip for use of the current data set screen 330. Here the tip field 322 states "Drag the dashed lines above to set heart rate ranges and the red and blue solid lines to set PQ and ST segments". The setting of heart rate ranges 335L, 335N, 335E and 335H is described above; the setting of PQ and ST segments is shown in FIG. 12.

The Save button 324 will save the parameters set using screen 330 to the IMD. The Close button 325 (or the X button in the upper right of the screen 330) will return to the Dataset screen for the most recently uploaded dataset. (from which the Edit Implant Parameters screen was activated by clicking on a beat). The Help button 327 provides access to instructions related to the screen 330, as well as access to the entire built in instruction manual similar to the Help menu 226e of FIG. 4.

The Print Parameters button 326 will allow the user to select the printing of any of the following:
  1. the current screen 330; or
  2. the values of all of the settable parameters for the IMD 5.

FIG. 11 is an enlargement of the PQ and ST segment parameter graphical user interface window 338 of the screen 330 of FIG. 10. The window 338 is used to set the start time and duration of the PQ and ST segment for the Fischell et al. ST shift algorithm described in U.S. Pat. No. 6,609,023. The display box 350 shows an enlarge format view of the beat selected from an electrogram segment of any of the screens 240, 260, 280, 300 or 400 of FIGS. 5 through 9. The vertical lines 352 and 353, that would typically be color coded (e.g. red), highlight the start and end of the PQ segment 351. Similarly, the vertical lines 355 and 356, that would be typically color coded (e.g. blue), highlight the start and end of the ST segment 354. The current values of the start time and duration of the PQ segment are shown in the boxes 361 and 362 respectively. The numbers in the boxes 361 and 362 would typically be color coded to match the lines 352 and 353. The current values of the start time and duration of the ST segment are shown in the boxes 363 and 364 respectively. The numbers in the boxes 363 and 364 would typically be color coded to match the lines 355 and 356. The start time 361 is the time from the start of the PQ segment marked with the line 352 to the peak of the R wave of the beat shown in the box 350. The start time 363 is the time from the peak of the R wave of the beat shown in the box 350 to the start of the ST segment marked with the line 355.

The start time and durations are adjustable with the graphical user interface in three ways:
  1. by dragging the lines 352, 353, 355 or 356 to the left or the right,
  2. by typing exact values in milliseconds in the boxes 361, 362, 363 or 364, or
  3. by clicking on the up or down buttons (with triangles) on the right side of the boxes 361, 362, 363 or 364.

The heart rate in beats per minute (BPM) corresponding to the R-R interval from the beat displayed in the box 350 from the previous beat is displayed in the field 357. The selection box 358 allows the beat in the box 350 to have vertical auto-scaling to account for variations in signal amplitude. The tip field 359 below the box 350 guides the user to "Drag Start and End of PQ segments (red lines) and Start and End-of-ST segment (blue lines) or enter the numbers in the boxes to the right to set PQ and ST segment timing."

Although the preferred embodiment of the programmer 68 of FIG. 1 uses start time and duration with respect to the R wave 365 as the patient specific parameters to specify sub-segments of a beat (e.g. the PQ segment 351 or ST segment 354), other means for specifying sub-segments are envisioned. These include:
  1. Start time and end time of the sub-segment; and
  2. End time and duration of the sub-segment.

It is also envisioned that the sub-segments need not be referenced to the R wave (i.e. the R wave is the reference feature) but could use the S wave 366, T wave 367 or J point 368 as the reference feature.

FIG. 12 is an enlargement of the PQ-ST segment test section 340T of screen 330 with the test function activated. The test function is activated by clicking in the box 341 labeled "Display PQ and ST Segment Detail for Each Beat." A colored box 342 highlights the PQ segment for each beat, and a different color box 345 highlights the ST segment for each beat. The colored boxes are typically color coded to match the PQ and ST start and end lines 352, 353, 355 and 356 of FIG. 11. For example, if the PQ segment start and end lines 352 and 353 are red, the colored boxes 342 would be red, if the ST segment start and end lines 355 and 356 are blue, the colored boxes 345 would be blue. The previous beat and next beat select buttons 346a and 346b change the beat shown in the window 350 of FIG. 11. The previous segment and next segment select buttons 348a and 348b change the electrogram segment shown in the display 340 (or 340T if the test function is activated). The previous and next segment select buttons 348a and 348b will move up and down the dataset display screen from which the beat for editing parameter was selected. For example, if the beat of box 350 of FIG. 11 was selected by clicking on the $7^{th}$ beat in the electrogram segment 244 of the view current data set screen 240 of FIG. 5, then the previous segment button 348a will bring into the test section 340, the electrogram segment above segment 244 (i.e. electrogram segment 243). Similarly, the next segment button 348b will bring into the test section 340, the electrogram segment below segment 244 (i.e., electrogram segment 245). Whatever number beat (i.e., $1^{st}$ beat, $2^{nd}$ beat, etc.) is highlighted when the previous or next segment button 348a or 348b is clicked, that same beat will be highlighted in section 340 and displayed in the box 350 of FIG. 11.

Figure 13:
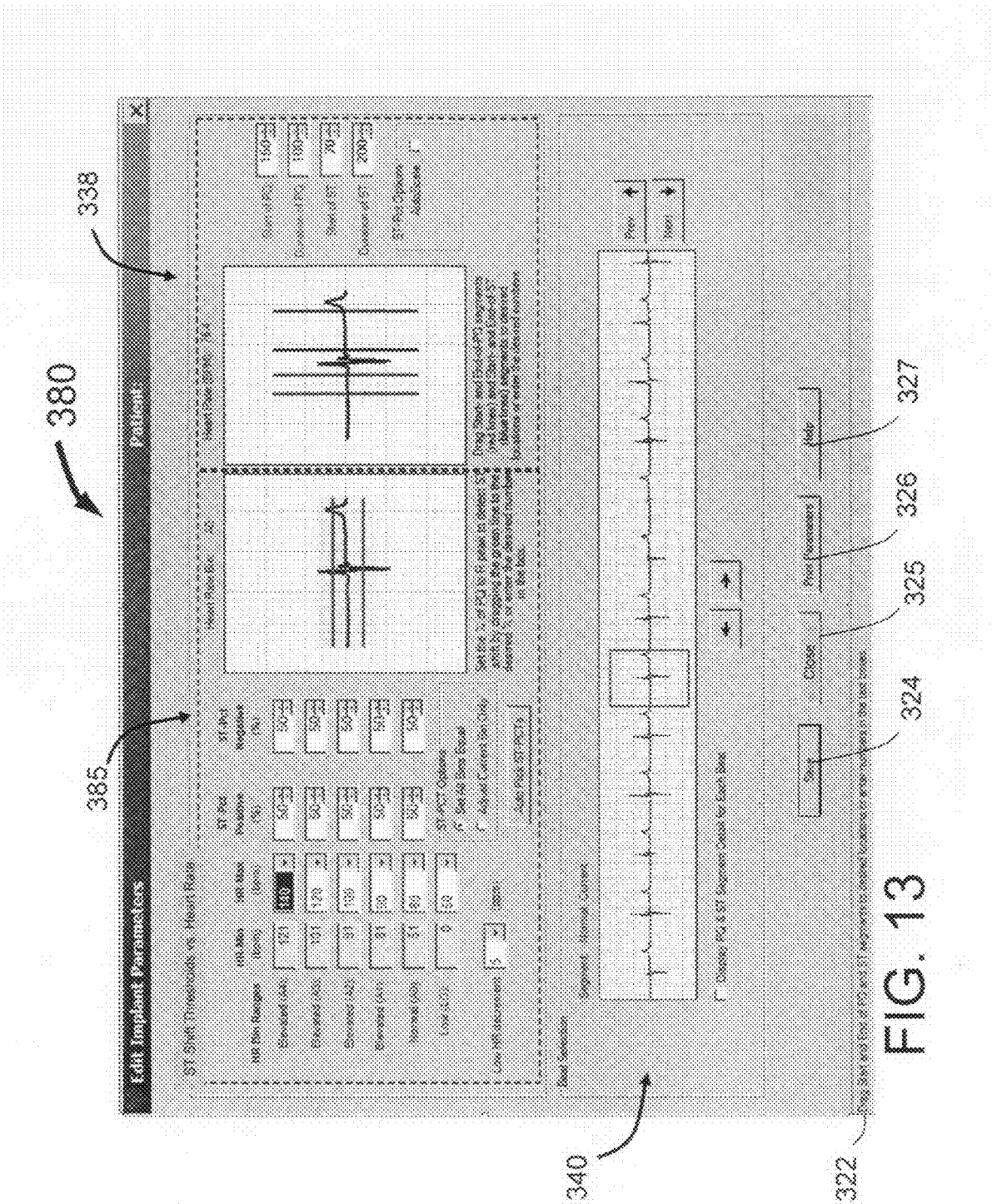
FIG. 13 is an example of the edit implant parameters screen used to manually set the key parameters used by the Fischell et al. ST shift algorithm.

FIG. 13 is the edit implant parameters screen 380 used to manually set the key parameters used by the Fischell et al. ST shift algorithm. The sections 338 and 340, the tip field 322 and buttons 324 through 327 are the same as in the screen 330 of FIG. 10. The section 385 also shown in FIG. 14 is the manual ST shift threshold graphical user interface.

Figure 14:
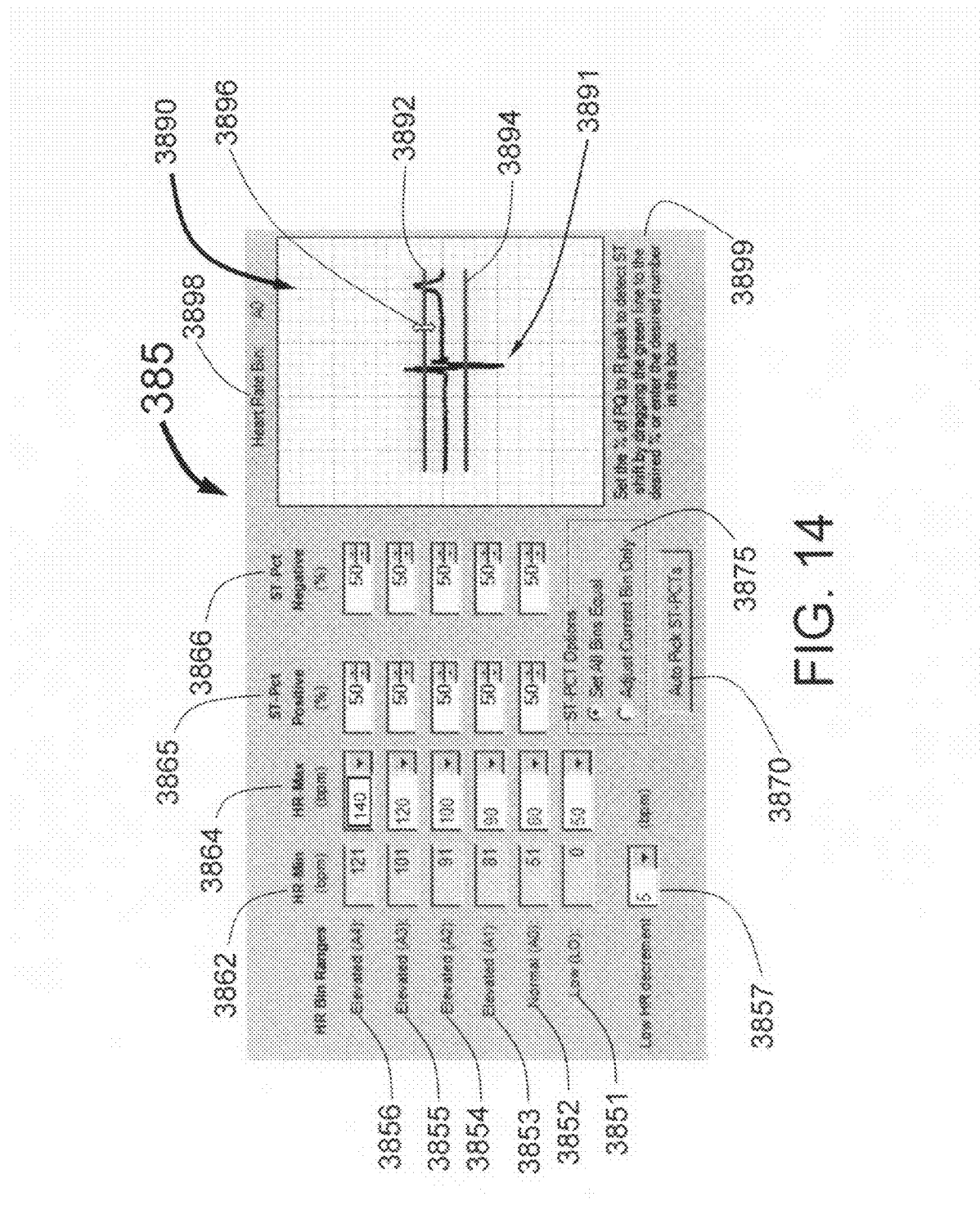
FIG. 14 is an enlargement of the manual ST shift threshold graphical user interface display and control buttons.

FIG. 14 is an enlargement of the manual ST shift threshold graphical user interface section 385 of FIG. 13. The section 385 includes the enlarged format beat display 3890 with the beat 3891 shown. The settings adjustable by the graphical user interface 385 are divided into settings for different heart rate bins. The bins are the low bin (LO) 3851, normal bin (A0) 3852 and elevated bins 3853 through 3856 (A1 through A4). The sets of boxes 3862 show the minimum heart rate and the sets of boxes 3864 show the maximum heart rate for each of the heart rate bins 3851 through 3856. The range in beats per minute (bpm) for each bin can be manually set by the user through entry of specific values into the maximum heart rate set of boxes 3864 or by selection from a menu by clicking on the down triangle to the right of the box.

The sets of boxes 3865 and 3866 are used to manually set the positive (3865) and negative (3866) percentage ST shift thresholds for the Fischell et al. ST shift detection algorithm described in U.S. Pat. No. 6,609,023. These numbers can be typed into the sets of boxes 3865 and 3866 or adjusted up or down with the up and down arrows to the right of each box. The field 3875 allows the user to lock all of the percentages for the sets of boxes 3865 and 3866 together if "Set All Bins Equal" is checked or to adjust each bin individually if "Adjust Current Bin Only" is checked.

The field 3898 shows that the threshold bars 3892 and 3894 are displaying the values for the A0 Heart rate bin. By placing the graphical user interface cursor 3896 over the threshold bar 3892 as seen in the FIG. 14, one can adjust the value of one or more Positive ST shift thresholds 3865 by simply dragging the threshold bar 3892 up or down. If "Set All Bins Equal" is checked in the field 3875, then the positive ST percentage thresholds 3865 for each heart rate bin 3851 through 3856 will adjust together. If "Adjust Current Bin Only" is checked in the field 3875, then only one heart rate bin (e.g. A0 shown in the field 3898) will be adjusted. Similarly, the negative percentage ST shift thresholds 3866 can be set by dragging the threshold bar 3894 up or down.

The tip field 3899 provides instructions on how to adjust the percentage ST shift thresholds, where the green lines referred to are the threshold bars 3892 and 3894.

Even from the manual ST shift threshold graphical user interface section 385 the Auto Pick function is accessible by selecting the Auto Pick ST-PCTs button 3870. This will initiate the same process as selecting the Auto Pick Thresholds button 339A of the screen 330 of FIG. 10. In this case the new thresholds selected by the programmer by analysis of recorded electrogram and statistical data will be displayed numerically in the threshold boxes 3865 and 3866.

The final element of the ST shift threshold graphical user interface section 385 is the Low HR decrement selection box 3857 which is used to prevent continuous alarm generation in the presence of frequent episodes of heart rate in the low heart rate bin. If a low heart rate is detected by the cardiosaver 5 of FIG. 1, the HR max value 3864 for the Low (LO) heart rate bin will then be decreased by the low heart rate decrement value 3857 to prevent additional detections whose alarms could be annoying and unnecessary as the event is already known.

FIG. 15 is an example of the physician's programmer Dataset Histogram screen 400 presenting statistical data relating to the daily variation in ST deviation (ST segment average voltage minus PQ segment average voltage) for each beat analyzed by the cardiosaver 5 of FIG. 1. The histogram display section 410 with histogram counts graph 420 shows the distribution of ST deviation for every beat analyzed by the cardiosaver 5 in the normal (A0) heart rate range, for the days with boxes checked in the date select field 415. The distribution is represented as the counts 422 of beats having ST deviation in closest to the bin labels 424 which represent a percentage of the electrogram signal amplitude. For example, the bin −5 would represent a negative ST deviation of 5% of the electrogram signal amplitude. For example, the electrogram signal amplitude could be the peak-to-peak QRS amplitude, the PQ to R peak height, the RMS electrogram voltage, or any other representative signal strength indicator. The electrogram signal amplitude can be extracted from each electrogram segment when it is collected by the cardiosaver 5 of FIG. 1, or it might preferably be a representative signal amplitude extracted from the baseline electrogram segment against which the currently collected electrogram segment is being compared as described by Fischell et al. in U.S. Pat. No. 6,609,023.

The A0 heart rate range is represented by the histogram shown in the display 410 because the A0 box is checked in the range selection field 411. The A0 heart rate range is the normal range as specified with the screen 330 of FIG. 10 or the screen 380 of FIG. 13. The range selection boxes in field 411 can be individually checked or unchecked. The Clear button 412 can be used to uncheck all the boxes in the field 411, and the All button 413 can be used to check all the boxes in field 411.

The histogram bars 425 of the display 410 show the number of beats whose ST deviation fell closest to one of the values of the ST deviation bins shown by the x axis scale 424. If two or more heart rate ranges are to be represented, each range would have a set of histogram bars in a different color according to the color key 414.

Similarly, the boxes in the date select field 415 can be individually checked or unchecked. The Clear button 416 can be used to uncheck all the boxes in the field 415, and the All button 417 can be used to check all the boxes in field 415. The graph type button 418 can be used to change the presentation of the graph 420 from a 2D bar chart to a line chart or other chart type. The update graph button 419 will update the chart 420 with any changes made in the fields 411 or 415.

The histogram trending section 430 of screen 400 contains the graph 440 which tracks the median daily ST deviation over the "weeks to display" time set by the selection box 436. In this example, 28 weeks of daily median ST deviation are displayed. The graph lines 431 through 435 inclusive would typically be lines of different colors in the graph 440 with the key 444 showing which color represents which heart rate range A0 through A5. In this case line 431 represents the normal heart rate range A0, and lines 432 through 435 represent the elevated heart rate ranges A1 through A5 respectively. The graph 440 is of great value to the diagnosing cardiologist as a downward trend of increasing ST depression, particularly at higher heart rates, may indicate a progressive narrowing of the patient's coronary artery. In this way the cardiosaver 5 acts as a continuous stress test that can present important diagnostic information to the physician. It is of greatest importance in patients with silent ischemia who would not otherwise have symptoms.

It is envisioned that an additional patient alert could be initiated by the cardiosaver 5 when there has been a significant absolute change in the median daily ST deviation. For example, a 10% absolute drop in median daily ST deviation in any band from baseline values set by the physician could initiate a SEE DOCTOR alert. The functionality to program the threshold for detection and baseline values would be programmed by the set alert button 446. Selecting the set alert button 446 would initiate a sequence of prompts to have the physician select baseline values and thresholds for detection associated with an alert. The type of alert might be settable using an additional field in screen 600 of FIG. 18, or the SEE DOCTOR alert might be the only one that can be enabled.

While the graph 440 displays the median daily ST deviation, other statistical data can be presented by the graph 440 by selecting from a list provided by the display selection box 447. Examples of other statistical information are median and standard deviation, mean, or mean and standard deviation.

The tip field 445 provides a tip for use of the dataset histogram screen 400. Here the tip field 445 states "Customize the Histogram Counts graph by changing the display parameters then clicking Update Graph".

The Close button 441 (or the X button in the upper right of the screen 400) will return to the screen from which the statistics or dataset statistics button was activated. The Print button 442 will print the data presented by the screen 400. The Help button 443 provides access to instructions related to the screen 400, as well as access to the entire built in instruction manual similar to the Help menu 226e of FIG. 4.

While the dataset histogram screen 400 of FIG. 15 shows the tracking of ST deviation over days and weeks, there are numerous other valuable heart signal parameters that could be similarly tracked and displayed with a pair of graphs such as the graphs 420 and 440. One such valuable heart signal parameter is the electrogram signal amplitude. For example, the QRS peak-to-peak voltage could be measured by the cardiosaver 5 of FIG. 1 for every beat the cardiosaver processes. Then the value of the QRS peak-to-peak voltage would be used to increment one bin in a daily histogram such as the histogram displayed for ST deviation in graph 420. The QRS peak-to-peak voltage could be tracked for all heart rates in a single histogram, or multiple histograms representing different heart rate ranges could be used. The values of median (or mean) QRS peak-to-peak voltage could be displayed in a graph similar to the graph 440. This is of particular importance where a significant drop in mean QRS amplitude has been shown to be indicative of potential rejection of a transplanted heart by Warnecke et al. in "Clinical Heart Transplantation without Routine Endomyocardial Biopsy" in the Journal of Heart and Lung Transplantation Vol. 11, No. 6, 1992. Here too, an EMERGENCY alarm or SEE DOCTOR alert could be used to warn the patient when such a drop in QRS amplitude is detected.

The button 448 is used to choose the specific heart signal parameter being presented by the dataset histogram screen 400. While ST deviation and QRS amplitude have been discussed above, other examples of heart signal parameters whose statistical data might be presented by the screen 400 include:

1. QRS width
2. number of PVCs per time period
3. T wave height
4. T wave width
5. R wave height
6. R wave width
7. ST segment voltage
8. ST segment slope It is envisioned that any or all or these example heart signal parameters could also have detection criteria for patient alerting programmed with the set alert button 446.

The multi-week graph 440 could also be the ideal place to show a time line of detected cardiac events and the cardiosaver programmed response to the detection (e.g. EMERGENCY alarm, SEE DOCTOR alert or record data only). The graph 440 of FIG. 15 shows two such events: a SEE DOCTOR alert 451 and an EMERGENCY ALARM 452. It is also envisioned that a time line of events might be presented with the main menu screen 220 of FIG. 4

Figure 16:
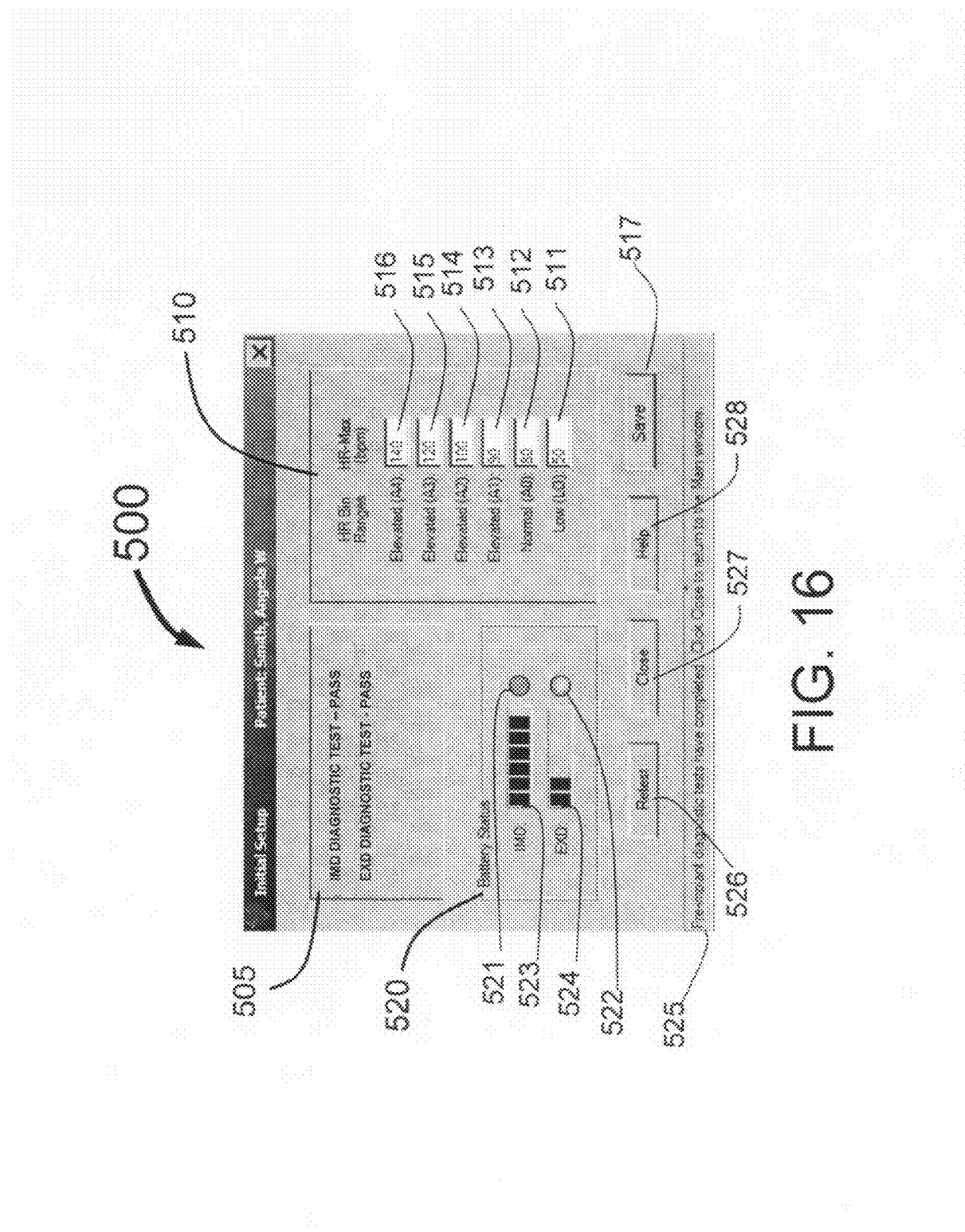
FIG. 16 is an example of the Initial Setup screen presented by the physician's programmer for the initial set up of the cardiosaver heart rate limits.

FIG. 16 is an example of the Initial Setup screen 500 presented by the physician's programmer 68 of FIG. 1 for checking the battery, and reading out and changing the current upper limits of the various heart rate bands for the IMD 5 of FIG. 1 before it is implanted into the patient. The heart rate limits section 510 includes the boxes 511 through 516 which display the current values of the maximum heart rate for each heart rate band where the use of heart rate bands is described by Fischell et al. in U.S. Pat. No. 6,609,023. The boxes 511 through 516 are also used to enter new values for the heart rate band upper limits. The box 511 is used to set the upper limit of the Low (LO) heart rate band, the box 512 is used to set the upper limit of the Normal (A0) heart rate band, and the boxes 513, 514, 515 and 516 are used to set the upper limits of the elevated heart rate bands A1, A2, A3 and A4. The A4 upper limit also serves to set the heart rate above which a high heart rate cardiac event is detected. If changes are made to the upper limits retrieved from the IMD when communication is established with the programmer, then the new upper limit will be sent to the IMD 5 by the use of the Save button 517. The upper limits of the heart rate bands can also be set using the Edit Implant Parameters screens 330 or 380 of FIGS. 10 and 13 respectively.

The status line 525 of the screen 500 indicates that pre-implant diagnostic tests (whose results are shown in section 510) have completed and that close will bring the user back to the Main window which is the screen 220 of FIG. 4.

The section 520 of the screen 500 shows the current battery status of the IMD 5 and EXD 60 of FIG. 1 The battery indicators 521 and 522 act as a colored light to indicate battery status where green is good, yellow is nearing the end of life, and red means change immediately. The IMD battery status bar 523 and EXD battery status bar 524 show graphically the amount of charge left in the battery.

The button 526 allows a retest of the EXD and IMD batteries and would be used to verify successful replacement of the EXD battery 59 of FIG. 1 which is typically replaceable. The retest button 526 would also be used if the there is a failure of either the IMD diagnostic test or EXD diagnostic test that is typically initiated following establishment of a programmer session. The section 505 displays the results from these tests. The tip field 525 indicates that the diagnostic tests whose results are shown in box 505 have been completed and that the close button 527 can be used to return to the main window (screen 220 of FIG. 4).

The Save button 517 will save any modifications made to the HR bin ranges to the IMD. The Close button 527 and the X button in the upper right of the screen 500 will return to the main window (screen 220 of FIG. 4). The Help button 528 provides access to instructions related to the screen 500 as well as access to the entire built in instruction manual similar to the Help menu 226e of FIG. 4.

Figure 17:
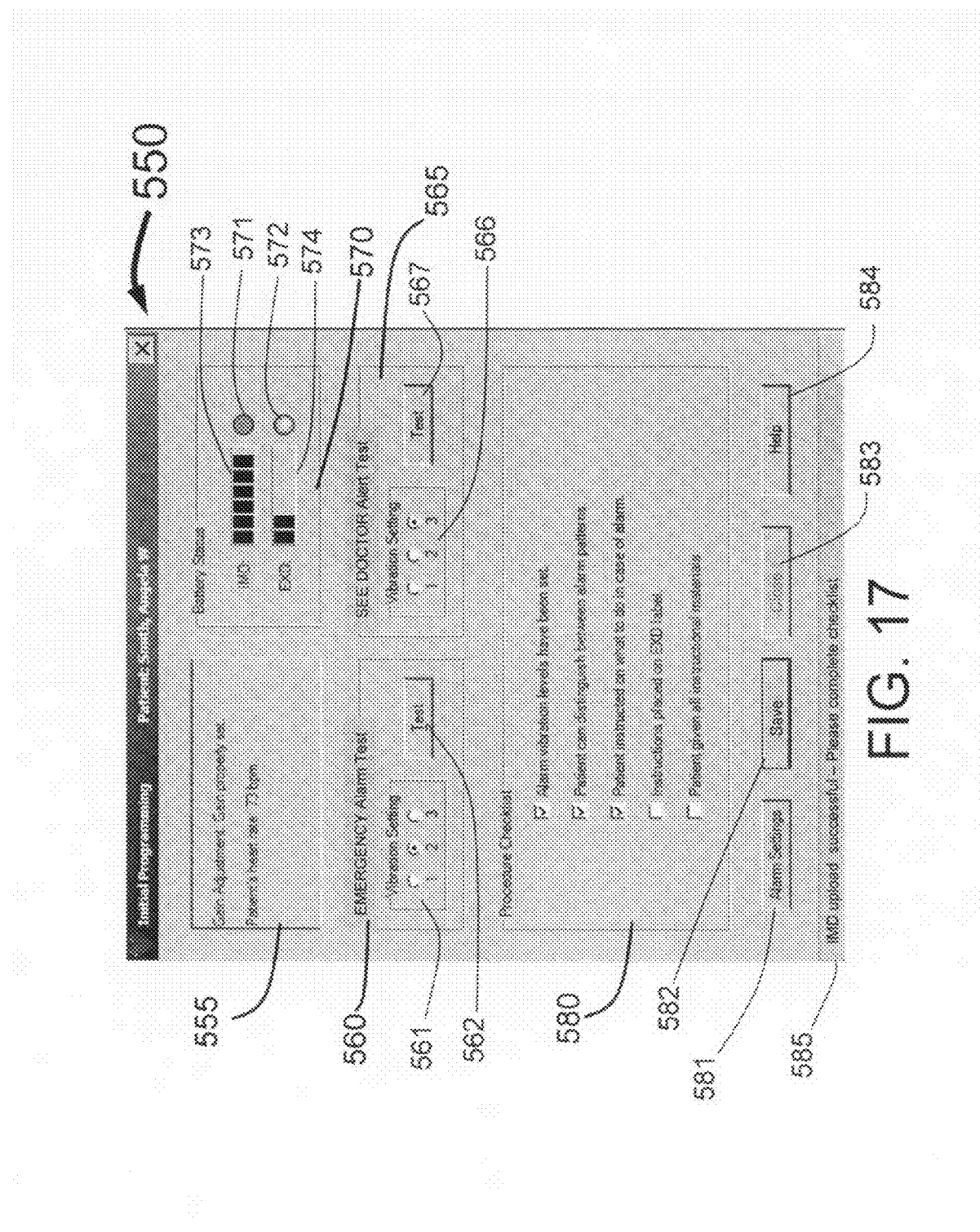
FIG. 17 is an example of an initial programming screen presented by the physician's programmer including the setting of vibration levels for the cardiosaver alarm signals and a check list to aid the medical practitioner.

FIG. 17 is an example of the initial programming screen 550 presented by the physician's programmer 68 of FIG. 1. The status box 555 displays the results of any IMD or EXD diagnostic testing. The screen 550 is used to set the initial programming for the IMD 5 following implant. The screen 550 includes sections 560 and 565 used to set and test vibration levels for the IMD 5 alarm signals. Section 560 is used to set and test the EMERGENCY alarm where the vibration setting field 561 selects the level (1, 2, or 3) for the intensity of the EMERGENCY alarm vibration. The test button 562 will turn on the EMERGENCY alarm for a short period of time (typically 10 to 60 seconds) allowing the patient time to learn to recognize the specific pattern associated with the EMERGENCY alarm and to ensure that the vibration setting (1, 2, or 3) is sufficient to be easily felt without being painful to the patient.

Section 565 is used to set and test the SEE DOCTOR alert where the vibration setting field 566 selects the level (1, 2, or 3) for the intensity of the SEE DOCTOR alert vibration. The test button 567 will turn on the SEE DOCTOR alert for a short period of time (typically 10 to 60 seconds) allowing the patient time to learn to recognize the specific pattern associated with the SEE DOCTOR alert and to ensure that the vibration setting (1, 2, or 3) is sufficient to be easily felt without being painful to the patient.

The section 570 of the screen 550 shows the current battery status of the IMD 5 and EXD 60 of FIG. 1 The battery indicators 571 and 572 act as a colored light to indicate battery status where green is good, yellow is nearing the end of life, and red means change immediately. The IMD battery status bar 573 and EXD battery status bar 574 show graphically the amount of charge left in the battery.

Figure 18:
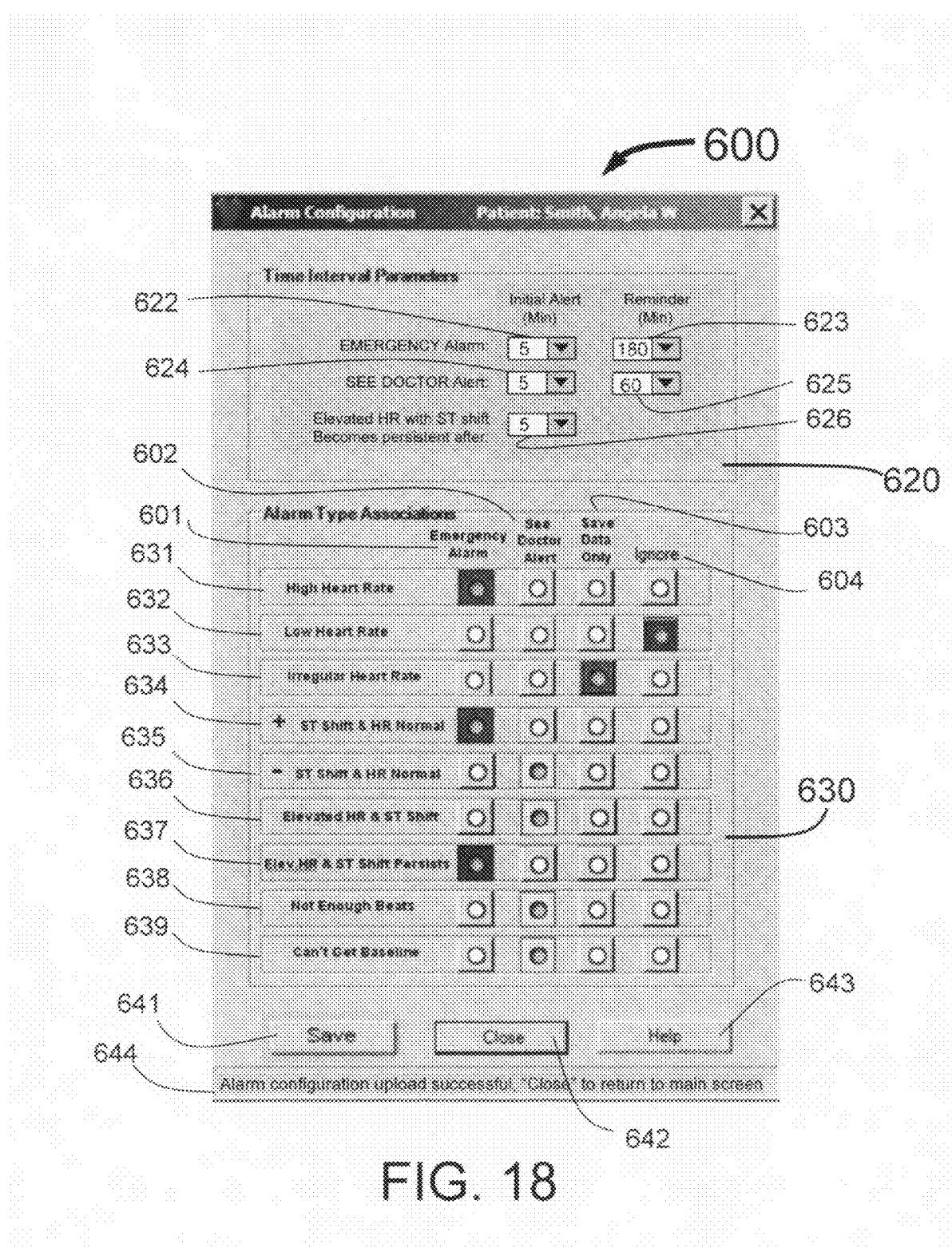
FIG. 18 is an example of the physician's programmer Alarm Configuration screen used to set the cardiosaver and external alarm device response to different detected cardiac irregularities.

The Alarm Settings button 581 opens the Alarm Configuration screen 600 of FIG. 18. The Save button 582 will upload the current settings of vibration selected in 561 and 566 to the IMD 5 of FIG. 1. The Close button 583 (or the X button in the upper right of the screen 550) will return to the main menu 240 of FIG. 4 without saving any changes in vibration setting if they have not been saved with the Save button 582. The Help button 584 provides access to instructions related to the screen 550 as well as access to the entire built in instruction manual similar to the Help menu 226e of FIG. 4.

The status line 585 of the screen 550 indicates that IMD upload using the Save button 582 has been successful and that the patient checklist 580 should be completed. Once all the boxes in the patient checklist 580 are checked, the Close button will be enabled. The purpose of the screen 550 is to require that the medical practitioner at least know that each of the items in the checklist 580 should be completed during IMD programming.

FIG. 18 is an example of the physician's programmer Alarm Configuration screen 600 used to set the response of the cardiosaver (IMD) 5 and external alarm device (EXD) 60 of FIG. 1 to different detected cardiac irregularities.

The Alarm Type Association section 630 allows selection of any of four different responses to a detected event. The responses each have their own column.

Column 601—"Emergency Alarm"
Column 602—"See Doctor alert"
Column 603—"Save Data Only" would not alert or alarm but save the relevant data.
Column 604—"Ignore" would ignore the detection and do nothing The screen 600 shows 9 different events that might be detected by the IMD 5 of FIG. 1. Each of the events has a corresponding row 631 through 639 where the response (any of 1 through 4 above) can be selected by clicking on the selection box in the appropriate column. In section 630 in this example of the alarm configuration screen 600, an EMERGENCY alarm is selected as the response to the high heart rate event 631, to an excessive positive ST shift event at normal heart rates 634, and to persistent excessive ST shift at an elevated heart rate 637. SEE DOCTOR alerts will be initiated for an excessive negative ST shirt event at normal heart rates 635, for an excessive ST shift event at an elevated heart rate 636, for not enough beats to process 638, and for an inability to obtain baseline electrogram segments 639. For irregular heart rate events 633, the "Save Data Only" box is selected, and for low heart rate events 632 the Ignore box is selected. These types of cardiac events are described by Fischell et al. in U.S. Pat. No. 6,609,023.

It is also envisioned that each alarm type in section 630 would use a different selection box color for each type of response to a detected event. For example, the selection of EMERGENCY alarm as the response would turn the selection box in the EMERGENCY Alarm column bright red, the selection of a SEE DOCTOR alert would turn the box bright yellow, the selection of "Save Data Only" would turn the box magenta, and the selection of "Ignore." Would turn the box blue.

Section 620 of the screen 600 includes the selection boxes 622, 623, 624, 625 and 626. The box 622 is used to set the initial alert duration of an EMERGENCY alarm by the IMD and EXD if the alarm disable button 52 of FIG. 1 is not used. The box 624 is used to set the initial alert duration after initiation of a SEE DOCTOR alert by the IMD and EXD if the alarm disable button 52 of FIG. 1 is not used. After the initial alarm/alert period, if the patient has not acknowledged the signal, a periodic reminder will be activated by the IMD for a reminder period to ensure that the patient takes the appropriate action. Box 623 is used to set the reminder time period during which the periodic reminder will be activated. An example of such a reminder for an EMERGENCY alarm would be to activate the EMERGENCY alarm for 30 seconds every 10 minutes for the reminder time period of 180 minutes shown in Box 623. Similarly, box 625 shows the reminder period for a SEE DOCTOR alert. Box 626 is used to set the time period after which an elevated heart rate with excessive ST shift will convert from a SEE DOCTOR alert to an EMERGENCY alarm. This box is only active if the SEE DOCTOR alert is selected for an elevated heart rate with excessive ST shift event in row 636 of the alarm type association section 630.

The Save button 641 will upload the parameters selected using the screen 600 to the IMD 5 of FIG. 1. The Close button 652 (or the X button in the upper right of the screen 600) will return to the main screen 220 of FIG. 4 without saving any changes in the alarm configuration settings. The Help button 643 provides access to instructions related to the screen 600 as well as access to the entire built in instruction manual similar to the Help menu 226e of FIG. 4.

The status line 644 of the screen 600 indicates that IMD upload using the Save button 641 has been successful and that the Close button will return to the main screen.

Figure 19:
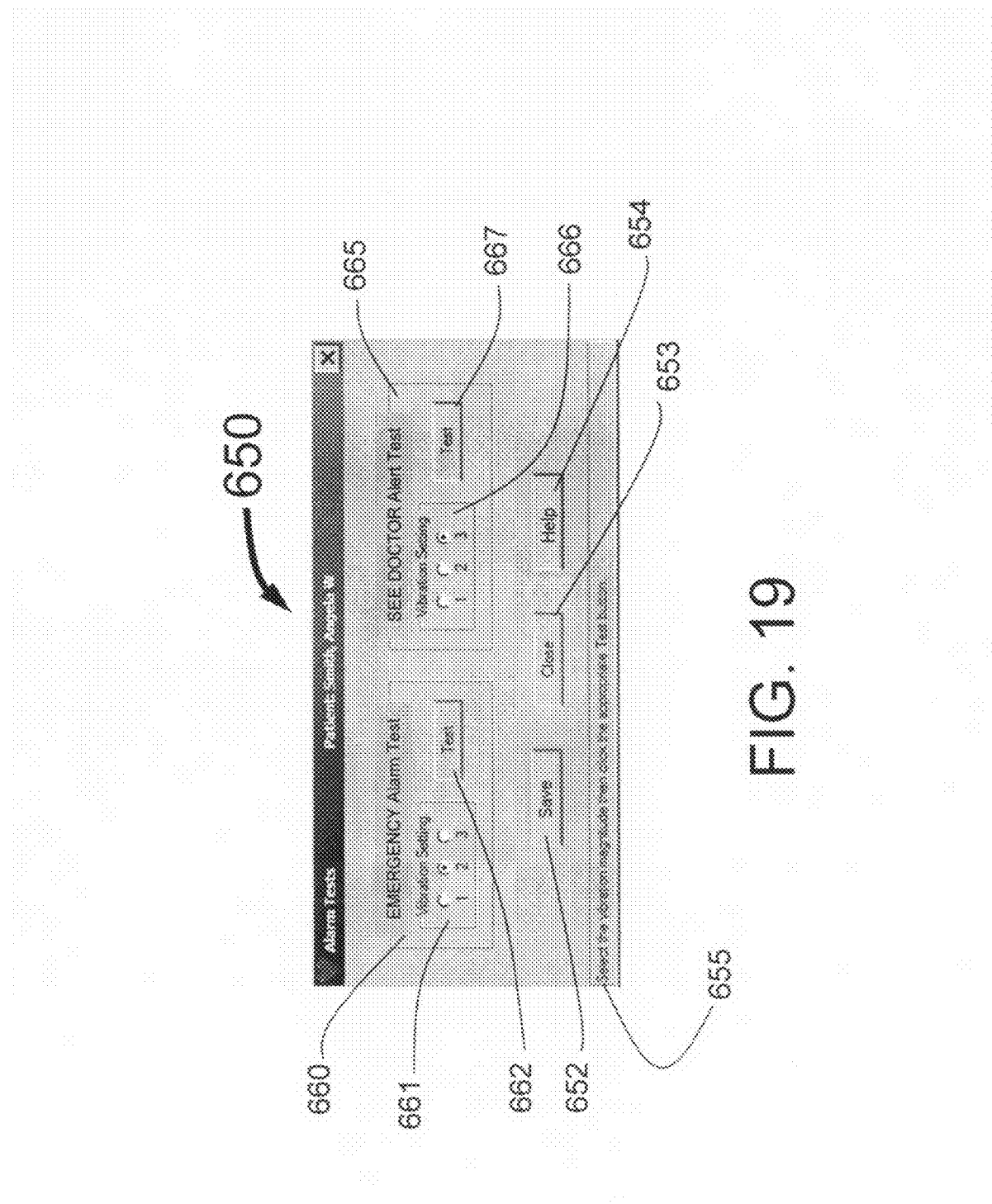
FIG. 19 is an example of the Alarm Tests screen accessed by the physician's programmer graphical user interface to allow the medical practitioner to change the vibration alarm signal settings and demonstrate them to the patient.

FIG. 19 is an example of the Alarm Tests screen 650 accessed by the physician's programmer 68 graphical user interface through the implant menu 226d of the main menu screen 220 of FIG. 4. The screen 650 is used to change the vibration alarm signal settings of the IMD 5 of FIG. 1 and to demonstrate the EMERGENCY alarm and SEE DOCTOR alert alarm signals to the patient.

The screen 650 includes sections 660 and 665 used to set and test vibration levels for the IMD 5 alarm signals. Section 660 is used to set and test the EMERGENCY alarm, where the vibration setting field 661 selects the level (1, 2, or 3) for the intensity of the EMERGENCY alarm vibration. The test button 662 will turn on the EMERGENCY alarm for a short period of time (typically 10 to 60 seconds) allowing the patient time to learn to recognize the specific pattern associated with the EMERGENCY alarm and to ensure that the vibration setting (1, 2, or 3) is sufficient to be easily felt without being painful to the patient.

Section 665 is used to set and test the SEE DOCTOR alert, where the vibration setting field 666 selects the level (1, 2, or 3) for the intensity of the SEE DOCTOR alert vibration. The test button 667 will turn on the SEE DOCTOR alert for a short period of time (typically 10 to 60 seconds) allowing the patient time to learn to recognize the specific pattern associated with the SEE DOCTOR alert and to ensure that the vibration setting (1, 2, or 3) is sufficient to be easily felt without being painful to the patient.

The Close button 653 (or the X button in the upper right of the screen 650) will return to the main screen 220 of FIG. 4 without saving any changes in vibration setting if they have not been saved with the Save button 652. The Help button 654 provides access to instructions related to the screen 650 as well as access to the entire built in instruction manual similar to the Help menu 226e of FIG. 4. The field 655 provides instructions for use of the screen 650 (e.g. Select the vibration magnitude than click the appropriate Test button) and is also used as a status field to confirm that new settings have been properly saved (uploaded) to the IMD 5 of FIG. 1.

It is also envisioned that the programmer 68 of FIG. 1 could have the capability to modify the pattern as well as the intensity for the EMERGENCY alarm and/or SEE DOCTOR alert. For example, the default EMERGENCY alarm might be three 250 millisecond vibration pulses with 500 milliseconds between pulses, repeated every 5 seconds (i.e., the vibration duration is 250 milliseconds, the vibration spacing is 500 milliseconds, and the repeat period is 5 seconds). It is envisioned that each of these times could be made adjustable through a programmer screen.

Finally, although most of the descriptions herein have dealt with a programmer for an implantable medical device, an external cardiosaver medical device using skin surface electrodes would require a programmer with the same functionality as that for an implantable cardiosaver. Therefore, it is envisioned that all of the aspects of the present invention programmer are usable with a medical device for detecting cardiac event whether implanted or not. The present invention programmer could function with either an implanted cardiosaver or an external cardiosaver with skin surface electrodes. Furthermore, although two-way wireless data communication is required for an implantable medical device, the present invention programmer could directly connect with wires to an external medical device. Such a connection would typically utilize a standard data communications interface (e.g. RS-232 serial, USB, parallel, firewire, etc.)

Various other modifications, adaptations, and alternative designs are of course possible in light of the above teachings. Therefore, it should be understood at this time that, within the scope of the appended claims, the invention can be practiced otherwise than as specifically described herein.

What is claimed is:

1. A programmer for an implantable medical device capable of detecting cardiac events in a human patient, the programmer including:
   two-way wireless data communication means with the implantable medical device; and
   a graphical user interface including a display and input means designed for use in programming a patient specific parameter;
   wherein the patient specific parameter is displayed on the graphical user interface in the form of a pictorial representation that is modifiable according to user input received through the input means; wherein the patient specific parameter pertains to ST shift.

2. The programmer of claim 1 further including electrogram segment display means.

3. The programmer of claim 1 further including a patient database.

4. The programmer of claim 1 further including an RF interface capable of two-way wireless data communication with the implantable medical device, the RF interface being designed to operate at a separation of greater than 6 inches between the implantable medical device and the programmer.

5. The programmer of claim 4 where the RF interface includes near field telemetry means capable of initiating two-way wireless communication between the implantable medical device and programmer.

6. The programmer of claim 1 where an external alarm device is used by the programmer for the two-way communication with the implantable medical device.

7. The programmer of claim 1 where the implantable medical device is implanted under the skin of the human patient.

8. The programmer of claim 1 where the ST shift related cardiac event is an acute myocardial infarction.

9. The programmer of claim 1 where the ST shift related cardiac event is ischemia at an elevated heart attack.

10. The programmer of claim 1 where the patient specific parameters include the start time for the ST segment with respect to a reference feature of each beat.

11. The programmer of claim 10 where the start time of the ST segment is programmed by entering values using the input means.

12. The programmer of claim 10 where the start time of the ST segment is programmed by selections from a menu using the input means.

13. The programmer of claim 10 where the start time of the ST segment is programmed by dragging an object on the graphical user interface using the input means.

14. The programmer of claim 10 where the start time of the ST segment is programmed by selecting up or down arrow buttons using the input means.

15. The programmer of claim 10 where the programmer further includes means to calculate the start times of the ST segment for a plurality of R-R interval values, the programmer also being designed to upload the start times of the ST segment for a plurality of R-R interval values to the implantable medical device through the two-way wireless data communication means.

16. The programmer of claim 15 where the start times of the ST segment for different R-R interval values is organized as a look-up table for the implantable medical device.

17. The programmer of claim 10 where the reference feature is the R wave.

18. The programmer of claim 10 where the reference feature is the S wave.

19. The programmer of claim 10 where the reference feature is the T wave.

20. The programmer of claim 10 where the reference feature is the J point.

21. The programmer of claim 1 where the patient specific parameters for the detection of ST shift related cardiac events includes the duration of the ST segment.

22. The programmer of claim 21 where the duration is programmed by entering values using the input means.

23. The programmer of claim 21 where the duration of the ST segment is programmed by selections from a menu using the input means.

24. The programmer of claim 21 where the duration of the ST segment is programmed by dragging an object on the graphical user interface using the input means.

25. The programmer of claim 21 where the duration of the ST segment are programmed by selecting up or down arrow buttons using the input means.

26. The programmer of claim 21 where the programmer further includes means to calculate the durations of the ST segment for a plurality of R-R interval values, the programmer also being designed to upload the durations of the ST segment for a plurality of R-R interval values to the implantable medical device through the two-way wireless data communication means.

27. The programmer of claim 26 where the durations of the ST segment for different R-R interval values is organized as a look-up table.

28. The programmer of claim 1 where the input means includes a data input device.

29. The programmer of claim 28 where the data input device is a keyboard.

30. The programmer of claim 28 where the data input device is a number pad.

31. The programmer of claim 1 where the input means includes a mouse.

32. The programmer of claim 31 where the input means includes a touch-screen.

33. The programmer of claim 31 where the input means includes a trackball.

34. The programmer of claim 31 where the input means includes a touch-pad.

35. The programmer of claim 31 where the input means includes a joystick.

36. The programmer of claim 1 further including an attached printer.

37. The programmer of claim 1 further including a bios password to prevent unauthorized access.

38. The programmer of claim 1 further including a pop-up login screen for user access.

39. The programmer of claim 1 further including indicators that there is an active data communications session established with a implantable medical device.

40. The programmer of claim 1 further including means to download heart signal data recorded by the implantable medical device.

41. The programmer of claim 40 further including means to calculate ST segment shift detection thresholds by processing the heart signal data downloaded from the implantable medical device.

42. The programmer of claim 41 where the heart signal data processed includes at least one histogram representation of the ST shifts of beats of the patient's heart analyzed by the implantable medical device.

43. The programmer of claim 40 where the heart signal data includes electrogram segments related to a detected cardiac event.

44. The programmer of claim 40 where the heart signal data includes periodically recorded baseline electrogram segments.

45. The programmer of claim 40 where the heart signal data includes recently recorded electrogram segments.

46. The programmer of claim 40 where the heart signal data includes at least one histogram representing the values of a heart signal parameter collected over a pre-set period of time.

47. The programmer of claim 46 where the pre-set period of time is programmable using the graphical user interface of the programmer.

48. The programmer of claim 1 wherein the pictorial representation comprises a representation of a biological signal and an icon oriented with respect to the representation of the biological signal so as to indicate the value of the patient specific parameter.

49. The programmer of claim 48 wherein the representation of the biological signal comprises a waveform.

50. The programmer of claim 49 wherein the waveform is an electrogram that is characterized by an R wave.

51. The programmer of claim 50 wherein the icon comprises a bar.

52. The programmer of claim 51 wherein the patient specific parameter pertains to the magnitude of a portion of the waveform and the bar is positioned with respect to the waveform so as to indicate the magnitude.

53. The programmer of claim 51 wherein the patient specific parameter pertains to a temporal fiducial point within the waveform and the bar is positioned with respect to the waveform so as to indicate the value of the temporal fiducial point.

54. The programmer of claim 53 wherein the temporal fiducial point is an offset from the R wave.

55. The programmer of claim 1 wherein the patient specific parameter pertains to the magnitude of an ST deviation detection threshold.

56. The programmer of claim 55 wherein the detection threshold pertains to a change in ST deviation relative to a baseline value.

57. The programmer of claim 55 wherein the pictorial representation is a bar that represents the ST deviation detection threshold.

58. The programmer of claim 55 further including means to download heart signal data recorded by the implantable medical device and means to calculate ST deviation detection thresholds by processing the heart signal data downloaded from the implantable medical device.

59. The programmer of claim 1 wherein the patient specific parameter is programmed by dragging an object on the graphical user interface using the input means.

60. The programmer of claim 1 wherein the patient specific parameter is programmed by selecting up or down arrow buttons using the input means.

61. A programmer for an implantable medical device capable of detecting cardiac events in a human patient, the programmer including: two-way wireless data communication means with the implantable medical device; a processor for computing a value of a patient specific parameter based at least in part on patient specific data, and a graphical user interface including a display and input means designed for use in programming the patient specific parameter; wherein the patient specific parameter is displayed on the graphical user interface in the form of a pictorial representation, and wherein the input means and processor are configured to enable a user to select the value of the patient specific parameter computed by the processor; wherein the patient specific parameter pertains to ST shift.

62. The programmer of claim 61 wherein the input means and processor are configured to enable a user to reject the value of the patient specific parameter computed by the processor.

63. The programmer of claim 62 wherein the input means and processor are configured to enable the user to manually select the value of the patient specific parameter.

64. The programmer of claim 61 wherein the graphical user interface includes an icon that enables a user to select the value of the patient specific parameter computed by the processor by manipulating the icon.

* * * * *